United States Patent
Kellenberger et al.

(10) Patent No.: US 8,933,073 B2
(45) Date of Patent: Jan. 13, 2015

(54) MACROLIDES AND THEIR USE

(71) Applicant: Basilea Pharmaceutica AG, Basel (CH)

(72) Inventors: Johannes Laurenz Kellenberger, Riehen (CH); Jürg Dreier, Witterswil (CH)

(73) Assignee: Basilea Pharmaceutica AG, Basel (CH)

( * ) Notice: Subject to any disclaimer, the term of this patent is extended or adjusted under 35 U.S.C. 154(b) by 0 days.

(21) Appl. No.: 14/163,683

(22) Filed: Jan. 24, 2014

(65) Prior Publication Data
US 2014/0142100 A1    May 22, 2014

Related U.S. Application Data

(63) Continuation of application No. 13/389,394, filed as application No. PCT/EP2010/061822 on Aug. 13, 2010.

(30) Foreign Application Priority Data

Aug. 13, 2009 (EP) .................................... 09167830

(51) Int. Cl.
A61K 31/706 (2006.01)
C07D 498/04 (2006.01)
C07H 17/08 (2006.01)

(52) U.S. Cl.
CPC .............. *C07D 498/04* (2013.01); *C07H 17/08* (2013.01)
USPC ........ 514/234.2; 514/338; 544/131; 544/127; 546/271.7

(58) Field of Classification Search
USPC ....................... 514/234.2, 338; 544/131, 127; 546/271.7
See application file for complete search history.

(56) References Cited

FOREIGN PATENT DOCUMENTS

| WO | 2004/080391 | 9/2004 |
|---|---|---|
| WO | 2006/067589 | 6/2006 |
| WO | 2006/084410 | 8/2006 |
| WO | 2007/060518 | 5/2007 |
| WO | 2007/060627 | 5/2007 |
| WO | 2008/106226 | 9/2008 |

OTHER PUBLICATIONS

The English translation of the Japanese Office Action, issued on Jul. 8, 2014, in the corresponding Japanese application No. 2012-524239.

*Primary Examiner* — Kristin Vajda

(57) ABSTRACT

The invention relates to macrolide compounds of formula (I),

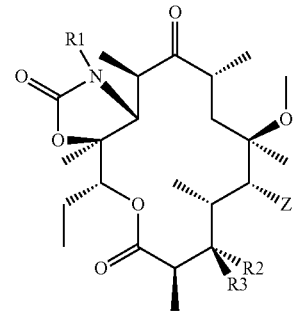

the use of said compounds as medicaments, in particular for the treatment or prevention of inflammatory and allergic diseases, pharmaceutical compositions containing said compounds and to processes for their preparation. The invention relates in particular to macrolide compounds with antiinflammatory activity mediated primarily through inhibition of phosphodiesterase 4 (PDE4) which makes them useful for the treatment and/or prevention of inflammatory and allergic diseases such as chronic obstructive pulmonary disease (COPD), asthma, rheumatoid arthritis, atopic dermatitis or inflammatory bowel disease or proliferative diseases such as cancer.

25 Claims, No Drawings

MACROLIDES AND THEIR USE

This application is a Continuation of application Ser. No. 13/389,394, filed Feb. 7, 2012, which is a National Stage Application of PCT/EP2010/061822 filed Aug. 13, 2010, which claims priority from European Patent Application 09167830.0 filed on Aug. 13, 2009. The priority of each prior mentioned application is claimed. Each of prior mentioned applications is hereby incorporated by reference herein in its entirety.

The invention relates to novel macrolide compounds, the use of said compounds as medicaments, in particular for the treatment or prevention of inflammatory and allergic diseases, pharmaceutical compositions containing said compounds and to processes for their preparation. The invention relates in particular to macrolide compounds with anti-inflammatory activity mediated primarily through inhibition of phosphodiesterase 4 (PDE4) which makes them useful for the treatment and/or prevention of inflammatory and allergic diseases such as chronic obstructive pulmonary disease (COPD), asthma, rheumatoid arthritis, atopic dermatitis or inflammatory bowel disease or proliferative diseases such as cancer.

Cyclic adenosine monophosphate (cAMP) is a key second messenger in cells. Increased levels of cyclic AMP are known to suppress cellular responses in various types of inflammatory and immune cells including lymphocytes, monocytes, macrophages, neutrophils, eosinophils, basophils and lung epithelial cells. Intracellular concentrations of cAMP are regulated by adenylyl cyclase and by cyclic nucleotide phosphodiesterases (PDEs). PDEs are a family of enzymes that inactivate cyclic nucleotides cAMP and cGMP through hydrolysis to AMP and GMP. The cAMP-specific enzyme PDE4 is the predominant enzyme in pro-inflammatory cells. PDE4 has been shown to be involved in inflammatory processes (cf. e.g. Lipworth B. J., Lancet (2005) 365, p. 167 or Giembycz M. A., Curr. Opin. Pharmacol. (2005), 5, p. 238). Therefore, inhibitors of PDE4 are useful in the treatment and/or prophylaxis of inflammatory and allergic diseases such as asthma, chronic bronchitis, emphysema, atopic dermatitis, urticaria allergic rhinitis, allergic conjunctivitis, psoriasis, rheumatoid arthritis, chronic obstructive pulmonary disease (COPD), septic shock, ulcerative colitis, Crohn's disease, adult respiratory distress syndrome and multiple sclerosis. PDE4 inhibitors are also useful for the treatment of proliferative diseases such as human cancer (cf e.g. Cancer Research, 2007, 67, p. 5248).

Numerous PDE4 inhibitors have been disclosed in the literature. (see for example J. O. Odingo, Expert. Opin. Ther. Patents, 2005, 15(7), 773; M. Hendrix, C. Kallus, Methods and Principles in Medicinal Chemistry (2004), Vol. 22 (Chemogenomics in Drug Discovery), 243-288 (Wiley-VCH)). Many of the known PDE4 inhibitors show dose-limiting side-effects such as emesis and headache.

Erythromycin derivatives having a substituted 11,12-cyclic carbamate substructure have been described in numerous publications (e.g. Antimicrob. Agents Chemother. 1989, 33, 78; Bioorg. Med. Chem. Lett., 1999, 9, 3075). Many of these macrolide derivatives have either a substituted or unsubstituted cladinose sugar moiety attached to the position 3 of the macrolactone ring or the 3-hydroxy group has been oxidized to a keto-group.

Compounds with a hydroxyl group in position 3 of the erythromycin scaffold are found as intermediates in the synthesis of various erythromycin-derivatives and are also disclosed in e.g. WO2004/013153. Formation of 3-acyl-derivatives is described in e.g. J. Med. Chem. 2003, 46, 2706.

Macrolide derivatives that are inhibitors of phosphodiesterase 4 have been disclosed in WO2008/017696.

Most of the molecules described in the references cited above have anti-infective activity. However, if erythromycin derivatives are foreseen for chronic treatment of diseases not caused by pathogenic bacteria, it is desirable to have compounds devoid of anti-infective activity in order to avoid the development of antibiotic-resistant bacteria. It has been reported that modifications of the desosamine moiety can lead to a loss of antibacterial activity. Various modifications of the desosamine sugar moiety of erythromycin derivatives have been described in the literature as exemplified by the following publications: WO2007/129646, WO2004/013153 and *Bioorg. Med. Chem.* 2007, 15, 3266.

Macrolide derivatives having a substituted 11,12-cyclic carbamate substructure and a modified desosamine sugar moiety have been disclosed in WO2006/087644, WO2007/054904, WO2008/106226 and WO2008/072034. Various 14-, 15- and 16-membered macrolides with a modified desosamine moiety and optionally a 11,12-cyclic carbamate substructure are also described in US2008/045585A1. However these compounds are not described as inhibitors of phosphodiesterase 4.

Surprisingly, it has now been found that certain macrolide compounds having a 11,12-cyclic carbamate substructure substituted with specific side chains, without having significant antibacterial activity, inhibit phosphodiesterases and in particular selectively inhibit PDE4, a newly found activity not described so far for this kind of molecules. These macrolides are therefore useful for the treatment and/or prevention of inflammatory and allergic diseases as well as proliferative diseases such as e.g. cancer. The molecules described herein are structurally distinct from currently known PDE4 inhibitors and therefore have the potential to overcome the above-mentioned side effects.

The present invention accordingly relates to macrolide compounds of formula I:

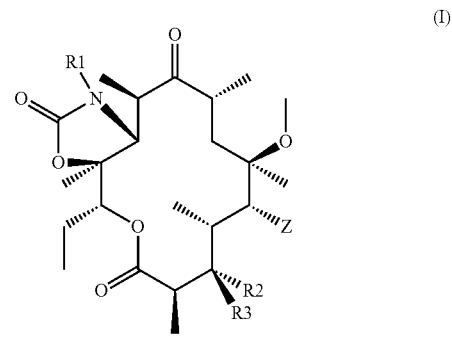

wherein
R1 is a residue —X-Q;
X is a bond or a linear group consisting of hydrogen atoms and 1 to 7 atoms selected from C, N, O and S, of which up to 2 atoms can be N and one atom can be O or S, one carbon atom can appear as a CO group and the sulfur atom can appear as an $SO_2$ group and two adjacent C atoms can be present as —CH=CH— or —C≡C— and which group X is unsubstituted or substituted;
Q is a residue -V-A1-L-A2-W or, if X does not represent a bond, may also be —NR6R7
V is an optionally substituted divalent aromatic or heterocyclic group;
W is optionally substituted aryl or heterocyclyl;

A1 and A2 are, independently of each other, either absent or a $C_1$-$C_4$alkylene group;

L is —O—, —S—, —SO$_2$—, —NH—, —CO—, —(CO)O—, —O(OC)—, —(CO)NH—, —NH(CO)—, —(SO$_2$)NH—, —HN(SO$_2$)—, —HN(CO)NH—, —O(CO)NH—, —NH(CO)O—, or can also be absent if A1 and/or A2 are present;

R2 is OR2a or

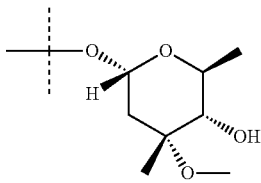

wherein

represents the linking bond;

R2a is hydrogen, acetyl, —(C=O)CH$_2$NR2bR2c, or —(C=O)CH$_2$CH$_2$NR2bR2c;

R2b and R2c independently of each other, are hydrogen or C1-C6 alkyl which can be substituted or unsubstituted and wherein up to two atoms can be N, O or S and one carbon atom can appear as C=O or, taken together with the nitrogen atom to which they are linked, form a 4-7 membered-ring of which up to two atoms can be N, O or S and one carbon can appear as C=O;

R3 is hydrogen or

R2 and R3 taken together with the carbon atom to which they are linked, represent a C=O group;

Z is

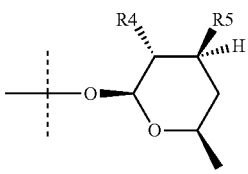

wherein

represents the linking bond;

R4 is —OR4a;

R5 is —NR5bR5c; or

R4 taken together with

R5 represent a group —O(CO)NR45-

R4a is hydrogen or C1-C6 alkyl which can be substituted or unsubstituted and wherein one or more single bonds can be replaced by double and/or triple bonds and where one carbon atom can appear as C=O and up to two atoms can be N, O or S;

R45 is hydrogen or C1-C6 alkyl;

R5b, R5c independently of one another, are hydrogen, C1-C6alkyl which can be substituted or unsubstituted, and up to two atoms of which can be N, O or S and where one carbon atom can appear as C=O, or —(C=O)heterocyclyl or, taken together with the nitrogen atom to which they are linked, form a 4-7 membered-ring of which up to two atoms can be N, O or S and one carbon can appear as C=O;

R6 and R7 are independently selected from hydrogen, methyl; from optionally substituted groups selected from aryl; aralkyl; heterocyclyl and heterocyclylalkyl groups, and one of R6 and R7 can also be a group -L-A2-W;

wherein alkyl groups may be substituted with one or more substituents selected from $C_1$-$C_4$alkoxy, $C_3$-$C_7$cycloalkyloxy or $C_3$-$C_7$cycloalkyl-$C_1$-$C_4$alkoxy, halogen, halogen substituted alkyl groups, cyano, nitro, amino, alkylamino, dialkylamino, alkylthio, mercapto, hydroxy, carbamoyl, carboxyl and oxo, and provided that R5 is not a dimethylamino group;

or a pharmaceutically acceptable salt, a N-oxide or an in vivo cleavable ester of said compound of formula (I).

Furthermore, the term "macrolide compound" is understood in the present invention to include pharmaceutically acceptable salts, in particular such acid addition salts, and N-oxides of compounds of formula (I), as well as in vivo cleavable esters.

The compounds of the invention exhibit substantial inhibitory activity towards phosphodiesterases (PDEs), in particular towards PDE4, in particular human phosphodiesterases and PDE4, which has been shown to be involved in inflammatory processes (cf. e.g. Lipworth B. J., Lancet (2005) 365, p. 167 or Giembycz M. A., Curr. Opin. Pharmacol. (2005), 5, p. 238). The use of the compounds according to the present invention for the treatment of diseases and disorders in a subject, selected from animals like e.g. mammals, and particularly humans which can be ameliorated or relieved by inhibition of phosphodiesterases, in particular phosphodiesterase 4 (PDE4) is therefore a further aspect of the present invention. Based on this activity the present compounds are particularly useful for the prevention and/or treatment of inflammatory diseases as well as for the treatment and/or prevention of allergic diseases and for the prevention and/or treatment of diseases associated with uncontrolled cellular growth, proliferation and/or survival of body cells of such subjects, e.g. cancer. A use for humans is preferred.

Particularly important examples of such diseases are chronic obstructive pulmonary disease (COPD), asthma, rheumatoid arthritis, atopic dermatitis, psoriasis or inflammatory bowel disease and said cancer diseases.

It is a particular advantage of the compounds of the present invention that they do not have any significant antibacterial activity and can therefore be used for the prevention and/or treatment of inflammatory diseases as well as for the treatment and/or prevention of allergic diseases and for the prevention and/or treatment of diseases associated with uncontrolled cellular growth, proliferation and/or survival in such subjects, e.g. cancer, as indicated above, without providing a risk of developing antibiotic-resistant bacteria during said use.

For the purposes of the present invention the terms "aromatic group" and "aryl" refer to aromatic groups with one or more preferably 6-membered nuclei and having from 6 to 14 carbon atoms. Examples are in particular phenyl, naphthyl, anthryl and phenanthryl. These groups may be further substituted with 1, 2, 3 or 4 substituents selected from, for example, alkyl such as defined hereinafter, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined hereinafter, halogen substituted alkyl groups such as difluoromethyl or trifluoromethyl, trichloroethyl, halogen substituted alkoxy groups such as difluoromethoxy, cyano, nitro, amino, alkylamino, dialkylamino, alkylthio, mercapto, hydroxy, carbamoyl, carboxyl group. In case more than one substituent is attached to the aryl group, these substituents can be identical or different from each other. Also encompassed by the scope of the present invention are different possible regioisomers (constitution isomers) of a specific group, for example "dimethoxy-phenyl" means that both methoxy substituents may be attached to the phenyl ring in the 2,3-position, the 2,4-position, the 2,5-position, the 2,6-position, the 3,4-position, the 3,5-position and the 3,6-position.

As used herein the term "heterocyclic group" or "heterocyclyl" refers to an unsaturated, partially unsaturated or saturated, unsubstituted or substituted 5- to 10-membered (mono- or bicyclic) heterocyclic ring system containing at least one hetero atom selected from the group consisting of sulfur, oxygen, and, preferably, nitrogen. Exemplary heterocyclic substituents include, but are not limited to, for example, the following groups: piperidinyl, morpholinyl, 2-, 3- or 4-pyridyl, pyrrolidinyl, piperazinyl, 1H-pyrazol-1-yl, 1H-imidazol-1-yl, 1H-imidazol-2-yl, pyrazinyl, pyrimidyl, pyridazinyl, pyrazolyl, triazinyl, thiazolyl, thiadiazolyl, oxadiazolyl, triazolyl, e.g. 1H-[1,2,4]-triazol-1-yl, 1H-tetrazolyl, 2H-tetrazolyl; thienyl, furyl (2-furanyl or 3-furanyl), 1H-azepinyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, tetrahydrothienyl, and the like, or condensed heterocyclic ring systems such as quinolinyl, e.g. quinolin-8-yl, quinolin-5-yl, quinolin-2-yl, quinolin-6-yl, quinolin-3-yl, isoquinolinyl(6-isoquinolinyl), quinazolinyl, 1H-benztriazolyl, 1H-imidazo[4,5-c]pyridinyl, 5H-imidazo[4,5-c]pyridinyl, 1H-imidazo[4,5-b]pyridin-1-yl, 3H-imidazo[4,5-b]pyridin-3-yl, 1H-pyrazolo[3,4-b]pyridinyl, 1,2,3,4-tetrahydro-quinolinyl, 1,2,3,4-tetrahydro-isoquinolinyl, thieno[2,3-b]pyridinyl, benzothiazolyl (e.g. 2-benzothiazolyl), 1H-benzoimidazolyl, 1H-indolyl, 1,2,3,4-tetrahydroquinolinyl, purinyl, e.g. 9H-purin-9-yl, 6-amino-9H-purin-9-yl, 2,6-diamino-9H-purin-9-yl, 1H-purin-6-yl, 1H-2,3-dihydroindol-1-yl, 2,1,3-benzoxadiazol-5-yl, 2,1,3-benzoxadiazol-4-yl, 1,3-benzodioxol-5-yl, 2,3-benzoxazolinyl, 1,2-dihydro-oxazolo[5,4-c]pyridinyl, 6-quinoxalinyl, 2-benzo[b]thien-3-yl, 3,4-dihydro-1H-2-oxo-quinolin-6-yl.

The heterocyclyl groups may be further substituted by one or more substituents. Such substituents include, for example, alkyl groups such as defined hereinafter, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined hereinafter, halogen substituted alkyl groups such as trifluoromethyl, trichloroethyl; halogen substituted alkoxy groups such as difluoromethyloxy; cyano, nitro, amino, alkylamino, dialkylamino, alkylthio, mercapto, hydroxy, carbamoyl, carboxyl, an oxo group. In case more than one substituent is attached to the heterocyclyl group, these substituents can be identical or different from each other. Different regioisomers are also included within the scope of the present definition, for example "dimethylpyridyl" means that both methyl substituents may be attached to the pyridyl at all chemically possible positions. For example both methyl substituents may be attached to the 2-pyridyl in the 3,4-position, the 4,5-position, the 5,6-position, the 3,5-position, the 3,6-position, and the 4,6-position. Both methyl substituents may be attached to the 3-pyridyl in the 2,4-position, the 2,5-position, the 2,6-position, the 4,5-position, the 4,6-position, and the 5,6-position. Both methyl substituents may be attached to the 4-pyridyl in the 2,3-position, the 2,5-position, the 2,6-position, and the 3,5-position.

Especially preferred substituents for the heterocyclyl groups are alkyl, alkoxy, oxo, halogen, amino, alkylamino or dialkylamino, wherein alkyl and alkoxy are as defined hereinabove.

Examples of preferred substituted heterocyclic rings are 1H-pyrimidin-2,4-dione, 1H,3H-pyrimidin-2,4-dione-5-methyl, 1H-pyrimidin-4-amino-2-on, 6-amino-9H-purin, 6-dimethylamino-9H-purin, 2,6-diamino-9H-purin, 6-amino-8-[(3-pyridinylmethyl)amino]-9H-purin, 4-amino-imidazo[4,5-c]pyridine, 4-methoxy-imidazo[4,5-c]pyridine, 1-ethyl-pyrazolo[3,4-b]pyridine, 4-phenyl-1H-pyrazol, 3-(pyridin-3-yl)-1H-pyrazol, 3-(pyridin-4-yl)-1H-pyrazol-1-yl, 3-(pyridin-3-yl)-1H-imidazol-1-yl, 3-(pyridin-4-yl)-1H-imidazol-1-yl, 3-(pyridin-3-yl)-1H-[1,2,4]triazol, 3-(pyridin-4-yl)-1H-[1,2,4]triazol and 2-oxo-1,2,3,4-tetrahydroquinoline, 3,5-dichloro-pyridin.

As used herein the term "alkyl" refers to branched or straight chain saturated hydrocarbon groups having preferably 1 to 6 carbon atoms. Such groups are for example methyl, ethyl, n-propyl, isopropyl, tertiary butyl, pentyl, hexyl and the like. Such alkyl groups may be further substituted with one or more substituents selected from, for example, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined below, halogen substituted alkyl groups such as difluoromethyl or trifluoromethyl, trichloroethyl, cyano, nitro, amino, alkylamino, dialkylamino, alkylthio, mercapto, hydroxy, carbamoyl, carboxyl, or oxo. If more than one substituent are present, these can be either identical or different from each other.

The term aliphatic group refers to branched or preferably straight chain hydrocarbon groups having preferably 1 to 6 carbon atoms, which can be saturated or unsaturated. Examples include those mentioned for alkyl, vinyl, n-propenyl, n-propinyl, butenyl groups, butadienyl, pentenyl groups, and the like.

The term "halogen" refers to fluorine, chlorine, bromine or iodine preferably fluorine and chlorine.

In the combinations "heterocyclylalkyl" and "aralkyl" the single parts "heterocyclyl", "ar", i.e. aryl, and "alkyl" have the meanings indicated above.

The term $C_1$-$C_4$alkylene group refers e.g. to methylene, ethylene, n-propylene, iso-propylene or n-butylene.

In formula I, R1 is a residue of formula —X-Q.

X is either a bond; i.e. is "absent", or a linear group consisting of hydrogen atoms and up to 7 atoms selected from C, N, O and/or S, of which up to 2 atoms can be N and one atom can be O or S, one carbon atom can appear as a CO group and the sulphur atom can appear as an $SO_2$ group. Two adjacent C atoms can also be present as —CH═CH— or —C≡C—. The group X can be unsubstituted or substituted. As already indicated, the spacer group X with up to 7 atoms may carry additional hydrogen atoms to saturate a C atom to form a methylene group or to saturate a N atom to form an amino group. Preferably, this spacer consists of 2 to 5 atoms selected from C, N, O and/or S.

Preferred groups X are:
$(CH_2)_n$, $(CH_2)_mOCH_2$, $(CH_2)_2NCH_3(CH_2)_2$, $(CH_2)_pCOO$, $(CH_2)_pCONH$; $O(CH_2)_p$ or $HN(CH_2)_p$, where n and p are 2, 3 or 4 and m is 0 or preferably 1, 2 or 3 and which are linked to the nitrogen atom of the cyclic carbamate via a carbon atom and $NH(CH_2)_n$ which is linked to the nitrogen atom of the cyclic carbamate via the nitrogen atom of said group, where n is as defined above. More preferably n is 2 or 3.

Particularly preferred groups X are n-butylene and, more preferably 1,2-ethylene, n-propylene or iso-propylene and $O(CH_2)_p$ or $HN(CH_2)_p$, where p is 3 or 4, preferably 3.

In formula I, Q is a residue of the formula -V-A1-L-A2-W. Alternatively and if X does not represent a bond, Q in formula I may also be —NR6R7.

V is an optionally substituted divalent aromatic or heterocyclic group, e.g. one of those specifically mentioned above.

In another preferred group of compounds of formula I, V is a divalent group of formula

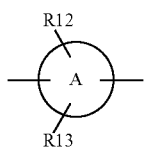

wherein

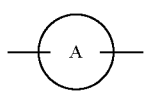

is a phenylene ring or a x-membered saturated or unsaturated divalent heterocycloaliphatic or heteroaromatic ring containing from 1, preferably from 2, to (x−1) carbon atoms with x being 5 to 8, preferably 5 or 6, and from 1 to (x−1), preferably to (x−2), in particular up to 4, more preferably up to 3, hetero atoms selected from the group consisting of sulfur, and preferably oxygen and nitrogen, R12 and R13 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen-substituted $C_1$-$C_4$alkoxy groups, cyano, nitro, amino, $C_1$-$C_4$alkylamino, di($C_1$-$C_4$)alkylamino, $C_1$-$C_4$alkylthio, mercapto, hydroxy, carbamoyl, a carboxyl group, an oxo group; or aryl or heterocyclyl, which may be unsubstituted or substituted with one or more of the above identified substituents other than aryl or heterocyclyl, or when both substituents R12 and R13 are located at adjacent carbon atoms of the ring $\textcircled{A}$, these two substituents, taken together with said adjacent carbon atoms, can also form a 5- or 6-membered aromatic or a x-membered saturated or unsaturated heterocycloaliphatic or heteroaromatic ring containing from 2 to (x−1) carbon atoms with x being 5 to 8, preferably 5 or 6, and from 1 to (x−2), preferably up to 4, more preferably up to 3, hetero atoms selected from the group consisting of sulfur and preferably, oxygen and nitrogen, and wherein V can have all together one to four substituents of the kind as defined for R12 and R13 and the free valences can be located either on one or on both rings of the group V.

Particularly preferred meanings of V include:

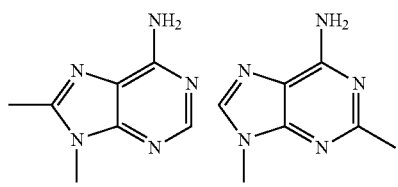

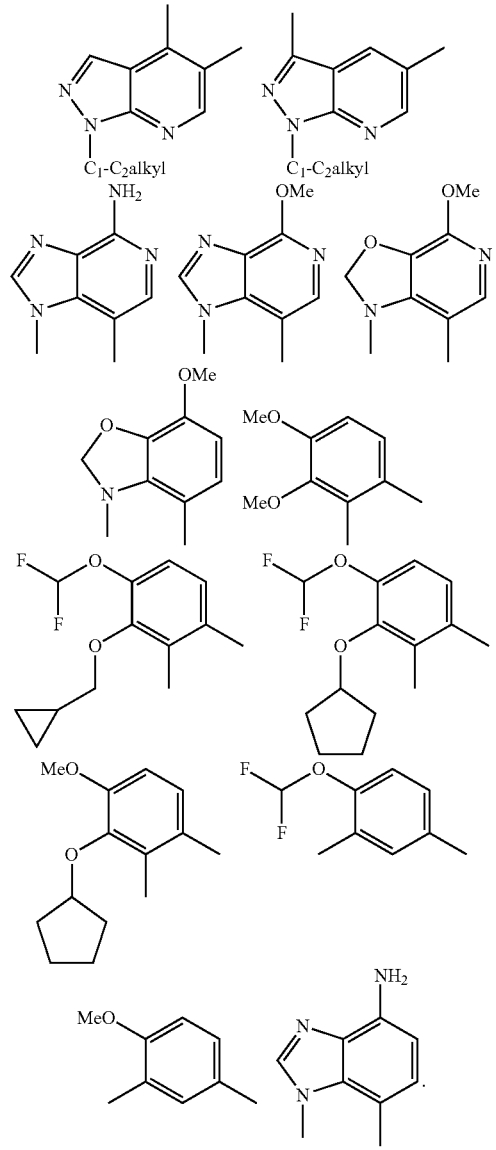

W in formula I can be either aryl or, preferably, heterocyclyl, both as explained above.

In a preferred embodiment of formula I, W represents a group of formula

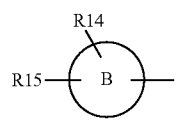

wherein

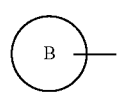

is a phenyl ring or a x-membered saturated or unsaturated monovalent heterocycloaliphatic or heteroaromatic ring containing from 1, preferably from 2, to (x−1) carbon atoms with x being 5 to 8, preferably 5 or 6, and from 1 to (x−1), preferably to (x−2), in particular up to 4, more preferably up to 3, hetero atoms selected from the group consisting of sulfur, and preferably oxygen and nitrogen, R14 and R15 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen-substituted $C_1$-$C_4$alkoxy groups, cyano, nitro, amino, $C_1$-$C_4$alkylamino, di($C_1$-$C_4$)alkylamino, $C_1$-$C_4$alkylthio, mercapto, hydroxy, carbamoyl, a carboxyl group, and an oxo group; or when both substituents R14 and R15 are located at adjacent carbon atoms of the ring Ⓑ, these two substituents, taken together with said adjacent carbon atoms, can also form a 5- or 6-membered aromatic or a x-membered saturated or unsaturated heterocycloaliphatic or heteroaromatic ring containing from 2 to (x−1) carbon atoms with x being 5 to 8, preferably 5 or 6, and from 1 to (x−2), preferably up to 3 hetero atoms selected from the group consisting of sulfur and preferably, oxygen and nitrogen, wherein W can have altogether one to four substituents of the kind as defined for R14 and R15 and the free valence can be located on either ring of the group W.

Particularly preferred examples of W are the following groups:

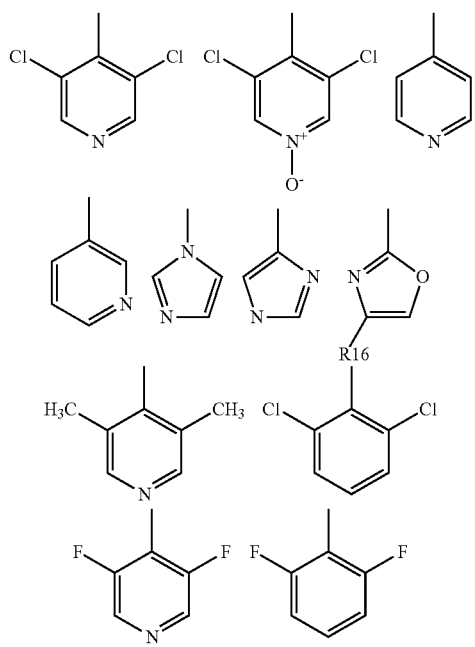

wherein R16 is hydrogen or $C_1$-$C_4$alkyl, in particular methyl.

In a group -V-A1-L-A2-W groups A1 and A2 are, in general, independently of each other either absent or a $C_1$-$C_4$alkylene group. L is generally selected from, —O—, —S—, —SO$_2$—, —NH—, —CO—, —(CO)O—, —O(OC)—, —(CO)NH—, —NH(CO)—, —(SO$_2$)NH—, —HN(SO$_2$)—, —HN(CO)NH—, —O(CO)NH—, and —NH(CO)O— in such group, but may also be absent if A1 and/or A2 are present.

In preferred examples of macrolide compounds according to the invention A1 and A2 are independently of each other either absent or represent a $C_1$-$C_2$alkylene group; and L is selected from —NH—, —(CO)NH— and —NH(CO)—; or is absent if A1 and/or A2 is present.

Particularly preferred are the compounds of formula (I) wherein

A1, A2 are independently of each other either absent or a $C_1$-$C_2$alkylene group;

L is —NH—, —(CO)NH— or —NH(CO)—;

V is a divalent group of formula

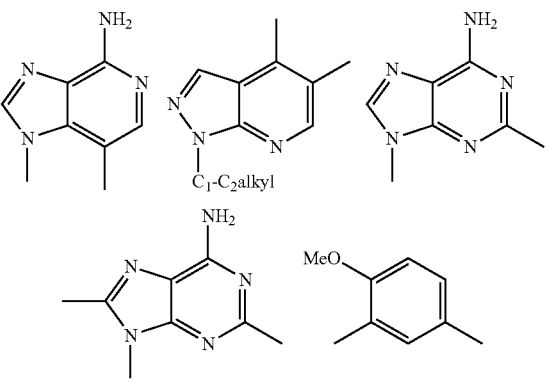

and

W is a group of formula

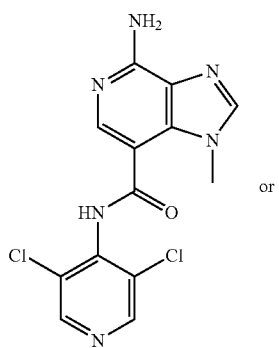

Also preferred are the compounds according to the present invention, in particular those mentioned in the preceding paragraph, wherein X is —CH$_2$—CH$_2$—CH$_2$— or —CH$_2$—CH$_2$—CH$_2$—CH$_2$—, in particular —CH$_2$—CH$_2$—CH$_2$—, or, preferably, —CH$_2$—CH$_2$—CH$_2$—NH— or —CH$_2$—CH$_2$—CH$_2$—O— linked to the residue Q via the NH group or O atom respectively.

Preferred examples of corresponding macrolide compounds according to the invention are compounds of formula I wherein Q has the following formula -continued

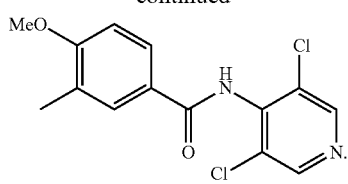

If X does not represent a bond in formula I, then Q may also be —NR6R7. In this case R6, and R7 may be independently selected from aryl, aralkyl, heterocyclyl and heterocyclylalkyl, e.g. as explained above, and one of R6 and R7 can also be a group -L-A2-W; wherein L, A2 and W have one of the meanings mentioned above.

Preferred examples according to the invention are furthermore compounds where R6 is aryl or aralkyl and has one of the following formulae

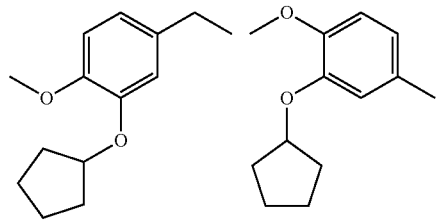

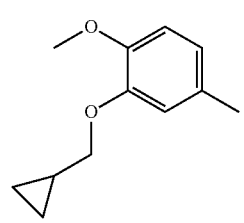

wherein

means a methoxy residue.

Preferred examples of corresponding macrolide compounds according to the invention are compounds of formula I wherein Q is a group —NR6R7 and has one of the following formulae

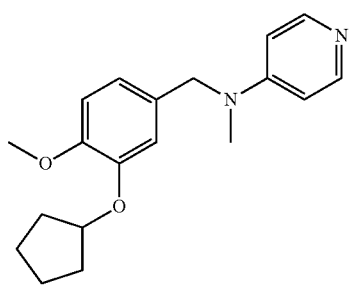

-continued

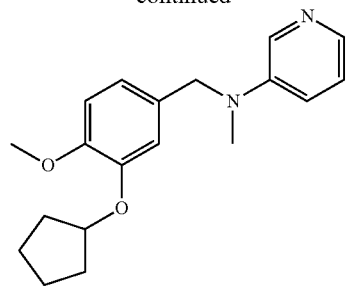

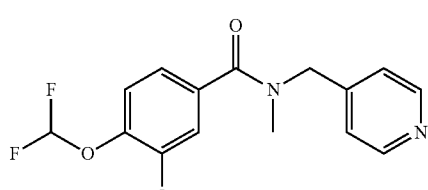

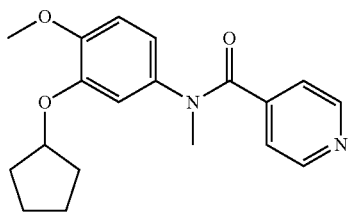

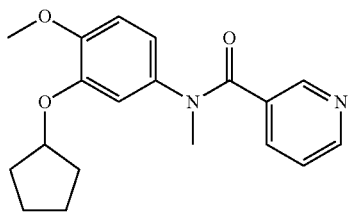

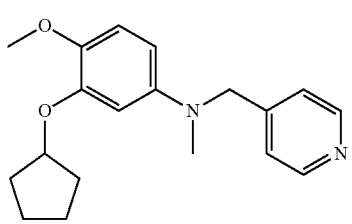

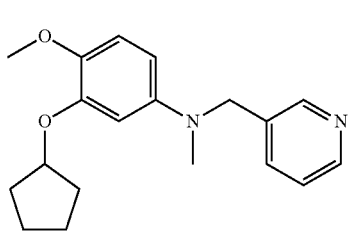

-continued

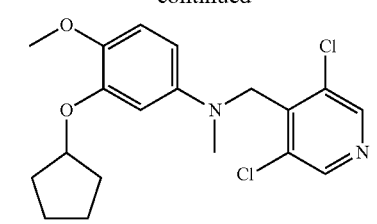

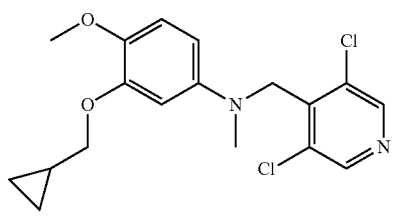

wherein

means a methoxy residue.

Preferred as well are compounds of formula I, wherein R5 is —NR5aR5b.

Further preferred embodiments of the compounds of the present invention include:

the compounds wherein R4a is hydrogen, C1-C6alkyl or vinyl, preferably hydrogen or C1-C6alkyl, the compounds, wherein R2 is

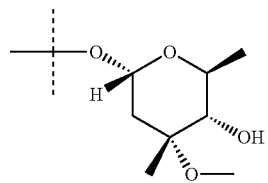

wherein

represents the linking bond;

the compounds wherein R2a is hydrogen;

the compounds, wherein R2 and R3 taken together with the carbon atom to which they are linked, represent a C=O group.

Specific examples of the compounds of the present invention include, e.g.:

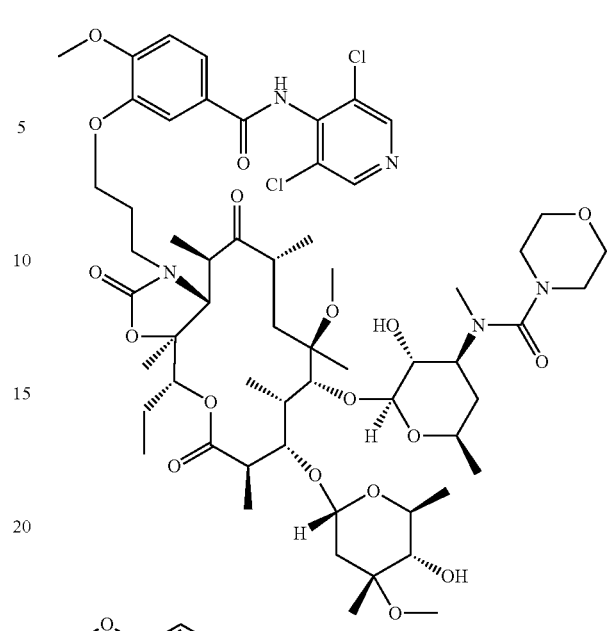

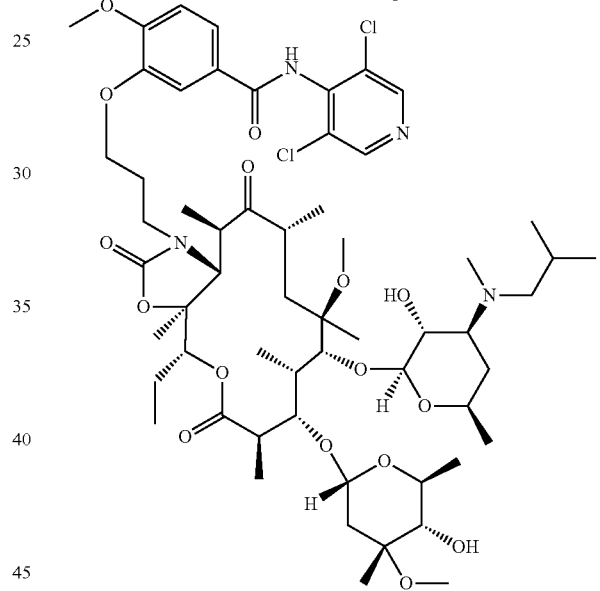

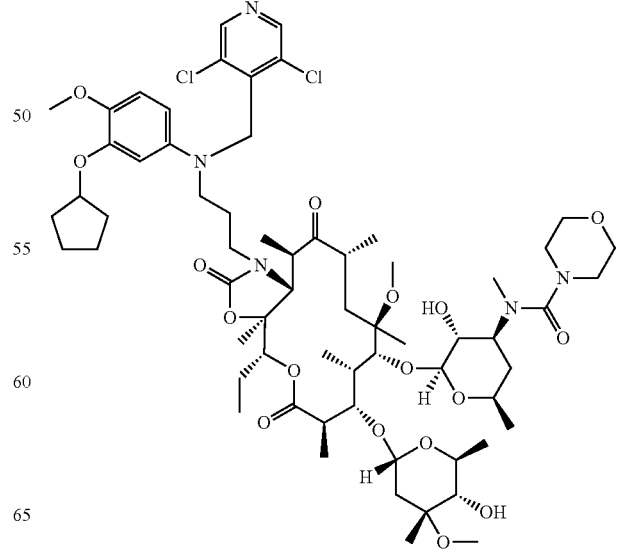

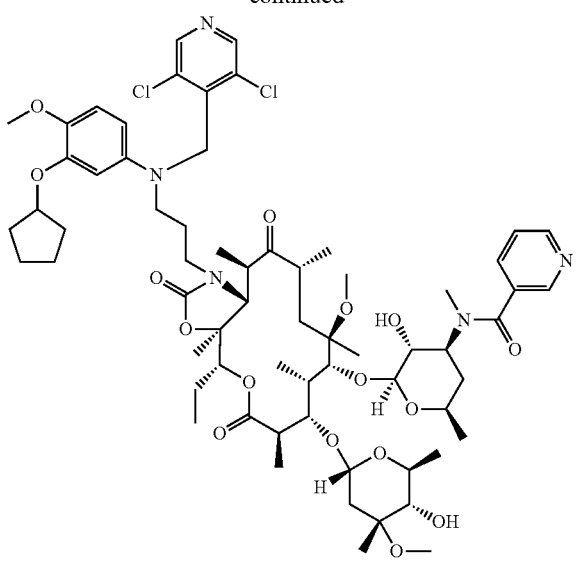
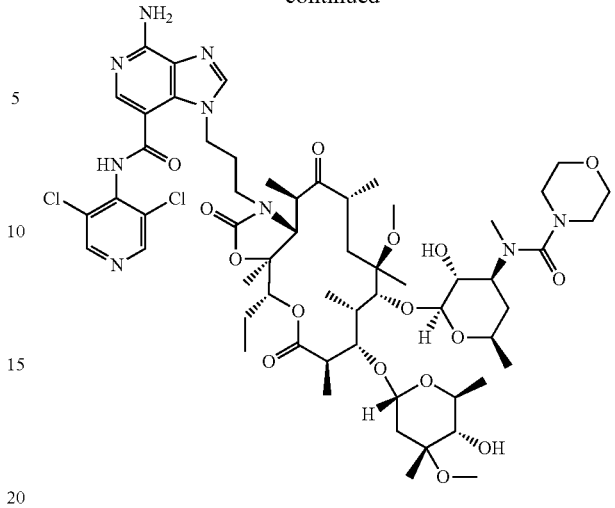
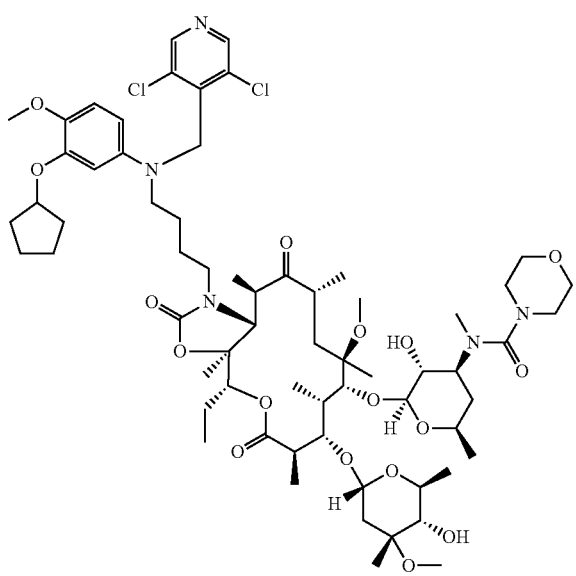
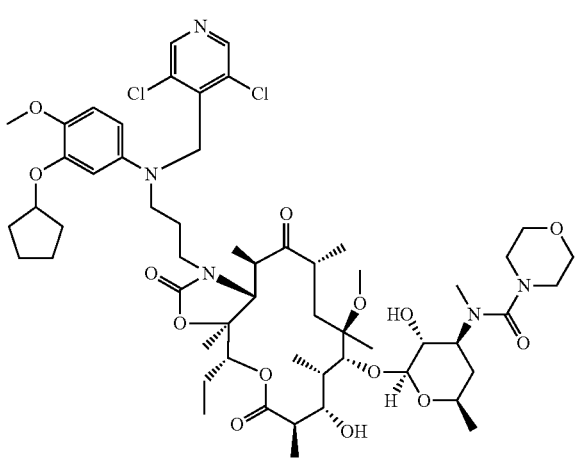

As already indicated above, the macrolide compounds of formula I can, if desired, also be present and used as pharmaceutically acceptable acid addition salts. Not only salts with inorganic acids, but also salts with organic acids come into consideration. Hydrochlorides, hydrobromides, sulfates, nitrates, citrates, acetates, trifluoroacetates, maleates, succinates, methanesulphonates, p-toluenesulphonates and the like are examples of such salts.

Further, the compounds of formula I can be in form of in vivo cleavable esters, for example esters with of the 2'-hydroxy group of the sugar moiety. Suitable esters are generally acetates, pivaloyl esters, tartrates, maleates, succinates, and the like.

The compounds of the present invention including their pharmaceutically acceptable acid addition salts or in vivo cleavable esters thereof are useful for the prevention and/or treatment of diseases such as chronic obstructive pulmonary disease (COPD), asthma, rheumatoid arthritis, atopic dermatitis or inflammatory bowel disease.

The compounds of the present invention and their pharmaceutically acceptable acid addition salts or in vivo cleavable esters thereof can also be used for the prevention and/or treatment of diseases such as chronic bronchitis, emphysema, urticaria, allergic rhinitis, allergic conjunctivitis, psoriasis, septic shock, adult respiratory distress syndrome and multiple sclerosis and for the treatment of human (+animal) diseases associated with uncontrolled cellular growth, proliferation and/or survival e.g. cancer.

The compounds in accordance with the invention can be used as medicaments. A further embodiment of the present invention are thus medicaments comprising compounds of formula I, their pharmaceutically acceptable acid addition salts, N-oxides or in vivo cleavable esters thereof for the treatment and prevention of inflammatory diseases or allergic diseases or diseases associated with uncontrolled cellular growth, proliferation and/or survival of cells belonging to a subject selected from animals, e.g. mammals, and preferably humans, for example, in the form of pharmaceutical preparations for enteral (oral) administration. The products in accordance with the invention can be administered, for example, perorally, such as in the form of tablets, film coated tablets, sugar coated tablets, hard and soft capsules, solutions, emulsions or suspensions, or rectally, such as in the form of suppositories, or parenterally e.g. by injection, or nasally, or by inhalation or transdermally, or locally for example by topical administration, preferably the compounds are administered topically or orally.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral, parenteral or topical dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as microcrystalline cellulose, calcium phosphate or lactose; disintegrating agents, such as starch, crosslinked carboxymethylcellulose sodium or crosslinked polyvinylpyrrolidone; and lubricating agents, such as talc, magnesium stearate, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, film coated tablets, sugar coated tablets and hard capsules there can be used, for example, lactose, maize starch or derivatives thereof, talc, stearic acid or its salts. Suitable carriers for soft capsules are, for example, vegetable oils, waxes, fats and semi-solid and liquid polyols (depending on the nature of the active substance). Suitable carrier materials for the preparation of solutions and syrups are, for example, water, alcohols, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavoring agents, salts for adjusting the osmotic pressure, buffers, coating agents and antioxidants.

The compounds of formula I and their pharmaceutically acceptable salts, in particular acid addition salts, or N-oxides or in vivo cleavable esters thereof can be used for parenteral administration and for this purpose are preferably made into preparations for injection as lyophilisates or dry powders for dilution with customary agents, such as water or isotonic common salt solution.

The compounds of formula I and their acid addition salts, N-oxides or in vivo cleavable esters thereof can be used for topical administration and for this purpose are preferably made into preparations as ointments, creams or gels.

For the treatment and/or prevention of inflammatory and allergic diseases in mammals, humans and non-humans, a daily dosage of about 10 mg to about 2000 mg, especially about 50 mg to about 1000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 10 mg, 100 mg, 250 mg, 500 mg and 1000 mg can be contemplated.

The preparation of compounds of formula I can e.g. be carried out according to schemes 1-6.

Compounds of the present invention can be prepared starting from clarithromycin. The preparation of compounds of formula II, III and IV wherein $Rp_1$ and $Rp_2$ are H, acetyl, benzoyl or any other suitable hydroxyl protecting group can be prepared by methods well known in the art (scheme 1). To obtain compounds of formula II wherein $Rp_1$ and $Rp_2$ are for example acetyl or benzoyl the 2'- and 4''-hydroxyl groups of commercially available clarithromycin can be protected either sequentially or simultaneously by reaction with a suitable acid anhydride or acid chloride as described in, for example, Baker et al., J. Org. Chem. 1988, 53, 2340-2345 and Kashimura et al., J. Antibiotics, 2001, 54, 664-678.

Compounds of formula II can then for example be transformed into compounds of formula IV in a similar way as described in Baker et al., J. Org. Chem. 1988, 53, 2340-2345. Compounds of formula IV are reacted with carbonyldiimidazole (CDI) in a solvent such as DMF or THF or a mixture thereof in the presence of a base such as for example NaH to form compounds of formula V. Compounds of formula V may also be prepared by prolonged treatment of compounds of formula II with CDI in a solvent such as THF and in the presence of a base such as NaHMDS at temperatures ranging from −40° C. to 50° C. Compounds of formula VII can be prepared by reacting compounds of formula V with an appropriate amine R1-NH2 in a solvent such as for example DMF, acetonitrile or a mixture of water and acetonitrile, optionally in the presence of a base such as for example DBU, at temperatures ranging from 0° C. to 80° C. (e.g. J. Med. Chem. 1998, 41, 4080). The intermediate VI may be isolated and subsequently subjected to cyclization in a solvent such as for example DMF, THF or acetonitrile in the presence of a base such as for example NaH or DBU, at temperatures ranging from 0° C. to 80° C.

Scheme 1

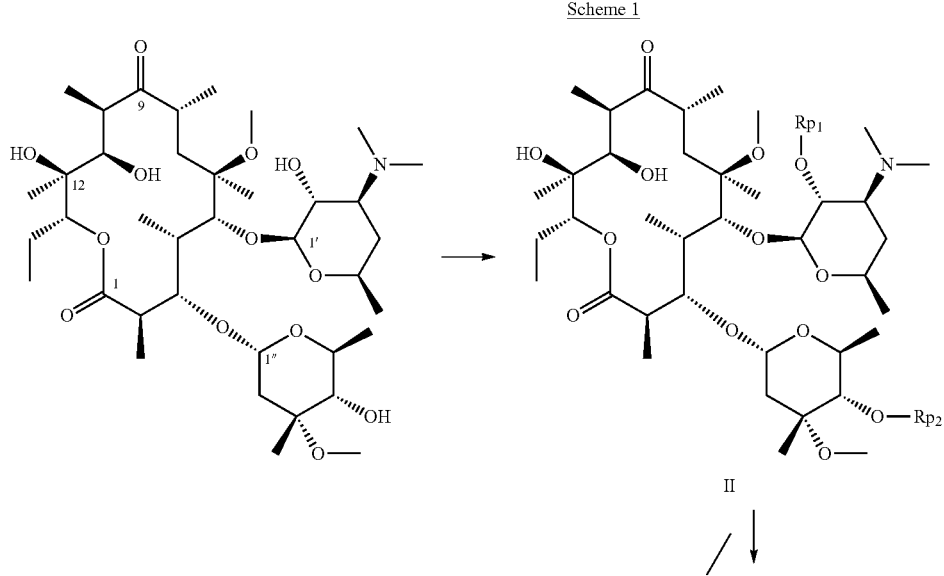

-continued
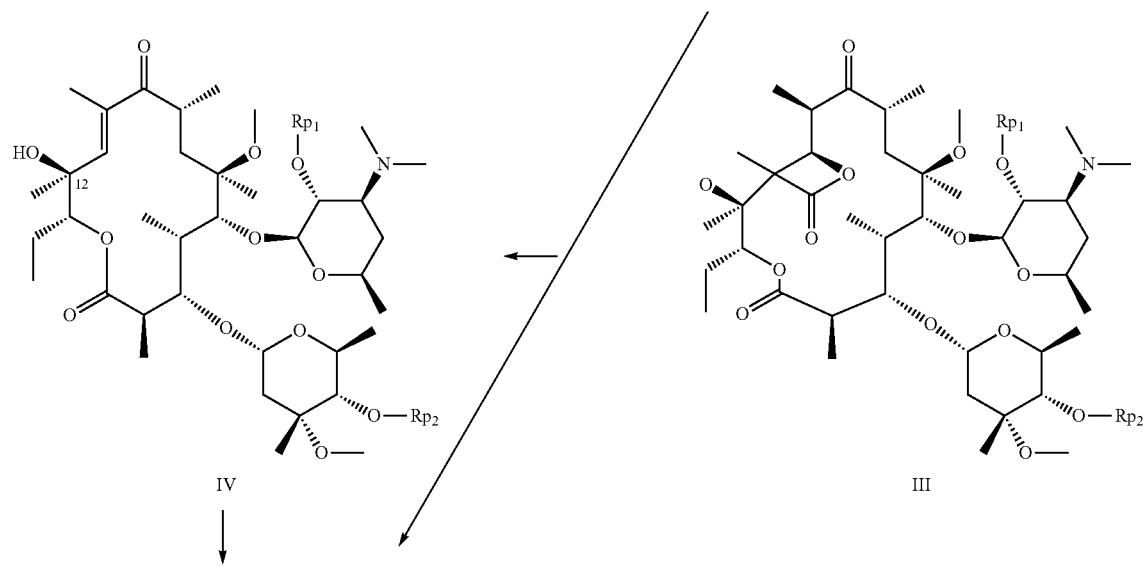
IV              III
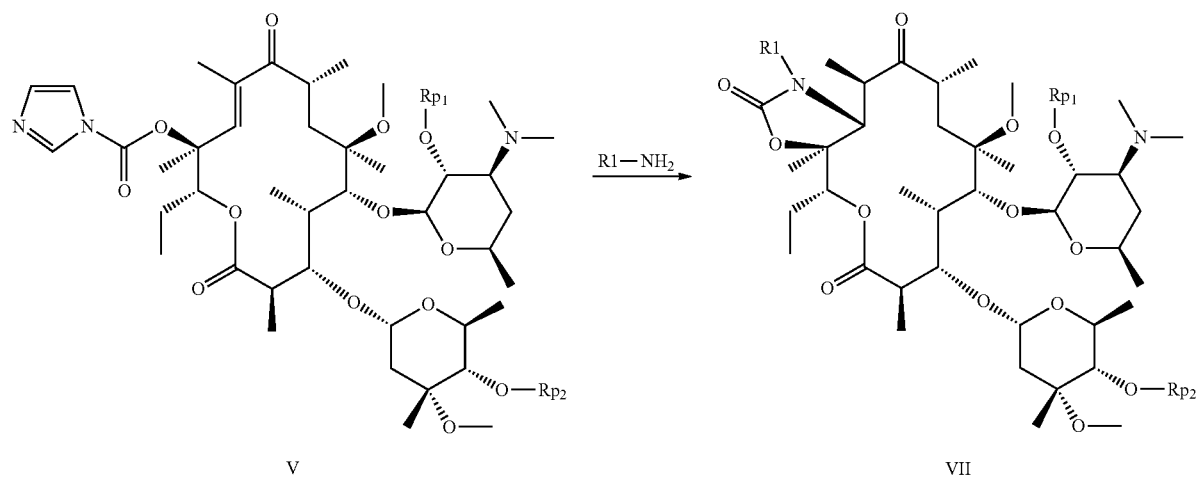
V               VII
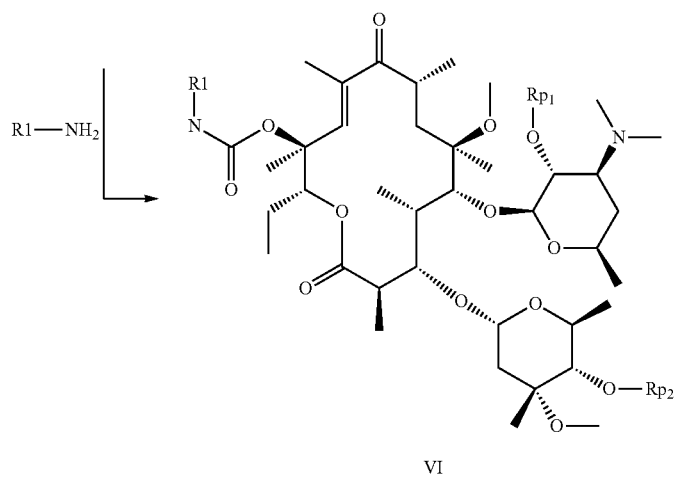
VI Scheme 2
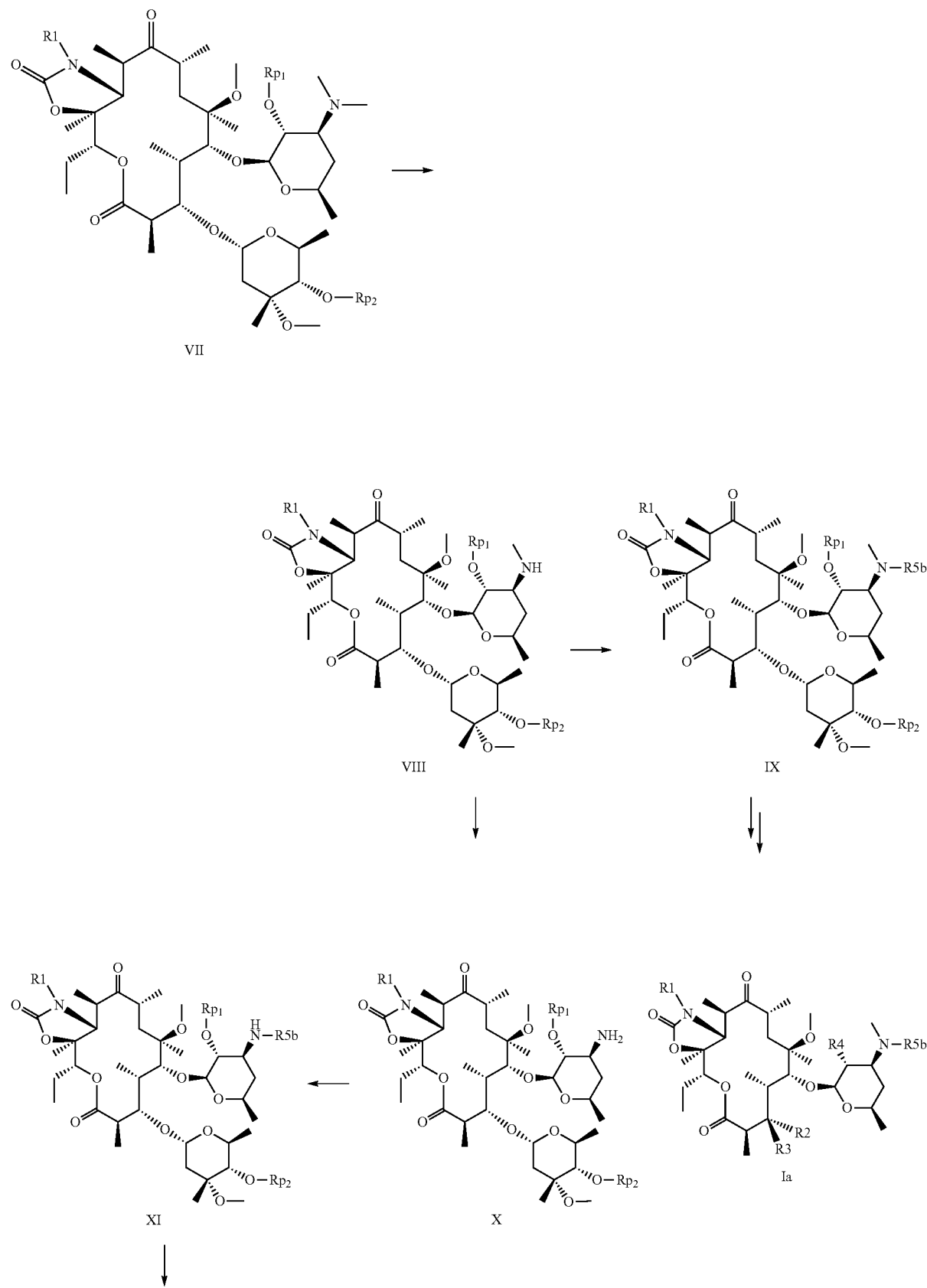

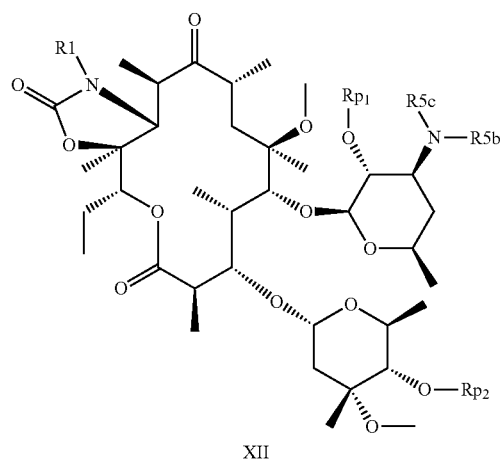

XII

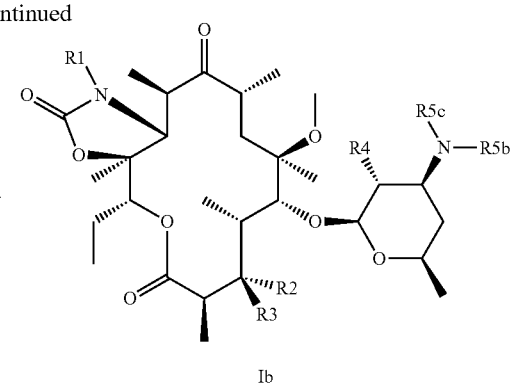

Ib

Compounds of formula Ia and Ib wherein R5b and R5c are as defined above but are not methyl may be prepared from compounds of formula VII (scheme 2). N-demethylation is for example performed using iodine under light or N-iodosuccinimide according to procedures described in the literature (J. Med. Chem., 1995, 38, 1793; J. Org. Chem. 2000, 65, 3875) to give compounds of formula VIII or of formula X. Substituents R5b and R5c are introduced e.g. by reductive amination using the appropriate aldehyde in the presence of a reducing agent such as $NaCNBH_3$ in a solvent such as methanol preferably at room temperature or by alkylation with an alkylhalide in the presence of base such as sodium hydride or sodium carbonate in a solvent such as DMF, acetonitrile, toluene or the like to give compounds of formula IX or XII. The two groups R5b and R5c can be introduced simultaneously or sequentially, preferably sequentially. Compounds of formula VIII, X and XI can also react with a substituted chloroformiate, substituted carbonyl chloride or carboxylic acid under standard conditions known in the art for the formation of amide bonds. Compounds of formula IX and XII can then be further modified according to any schemes 3-6 to give, after deprotection if necessary, compounds of Ia or Ib.

Compounds of general formula Ic where in R4 is O—R4a may be prepared from compounds of general formula VII. The protecting group Rp1 can be removed following procedures described below or according to procedures described in e.g. T. W. Green et al., Protective Groups in Organic Synthesis, John Wiley & Sons, 1999. The hydroxyl group in position 2' of compounds of formula XIII can be alkylated following methods known in the art, for example by treatment with an alkylhalide in the presence of a base such as sodium hydride, sodium carbonate or potassium carbonate in a solvent such as DMF, THF, DMSO, acetone or a mixture thereof to give compounds of formula XIV (scheme 3). Compounds of formula XIII can also react with a substituted chloroformiate, substituted carbonyl chloride or carboxylic acid under standard conditions known in the art for the formation of ester bonds to give compounds of formula XIV. Compounds of formula XIV can then be further modified according to any of schemes 2, 4, 5 and/or 6 to give, after deprotection if necessary, compounds of general formula Ic.

Scheme 3

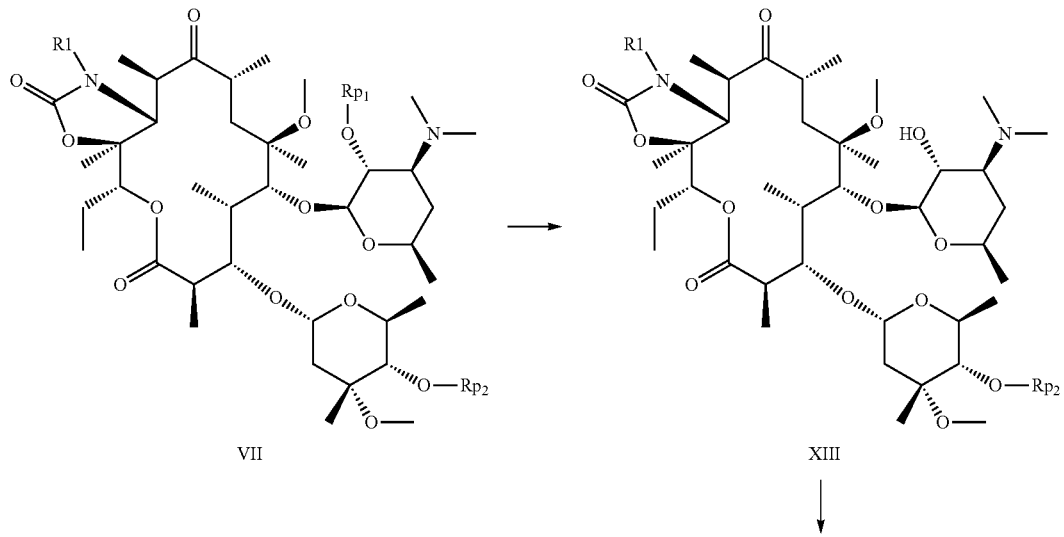

VII    XIII

-continued
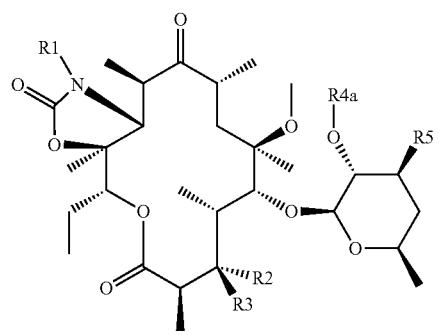
Ic
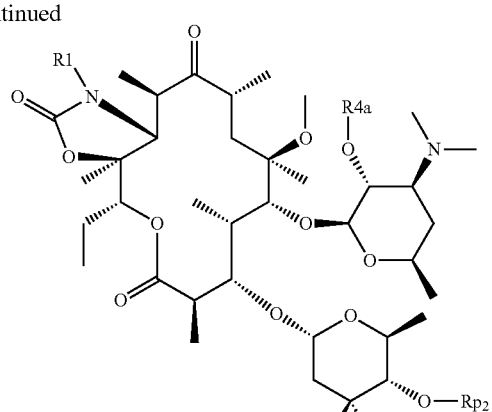
XIV
Compounds of formula Id may be prepared according to any of the schemes 1-6 and subsequent deprotection if necessary, as summarized in scheme 4 starting from compound XV (Bioorg. Med. Chem. 2007, 15, 3266). Alternatively, compounds of formula Id are prepared starting from compound VII according to methods similar to those described in Bioorg. Med. Chem. 2007, 15, 3266.

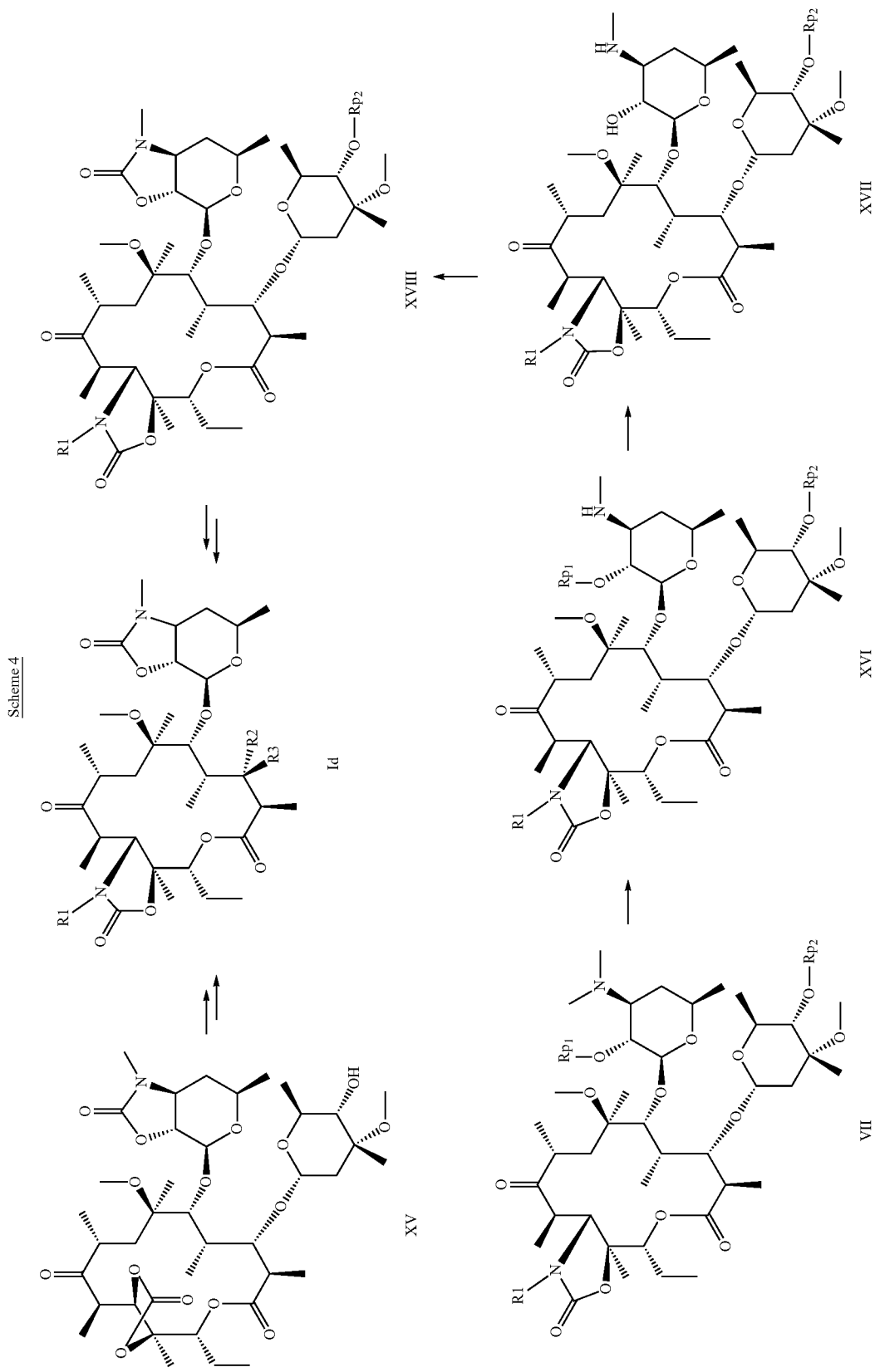

Compounds of formula Ie may be synthesized starting from compound XIX (J. Med. Chem. 1998, 41, 4080). The compound of formula XIX is then modified according to any of the schemes 1-6 to give, after deprotection if necessary, compounds of general formula Ie (scheme 5). Alternatively, compounds of formula Ie can be prepared starting from compound of formula VII according to methods well known in the art (e.g. WO03/072588).

Scheme 5

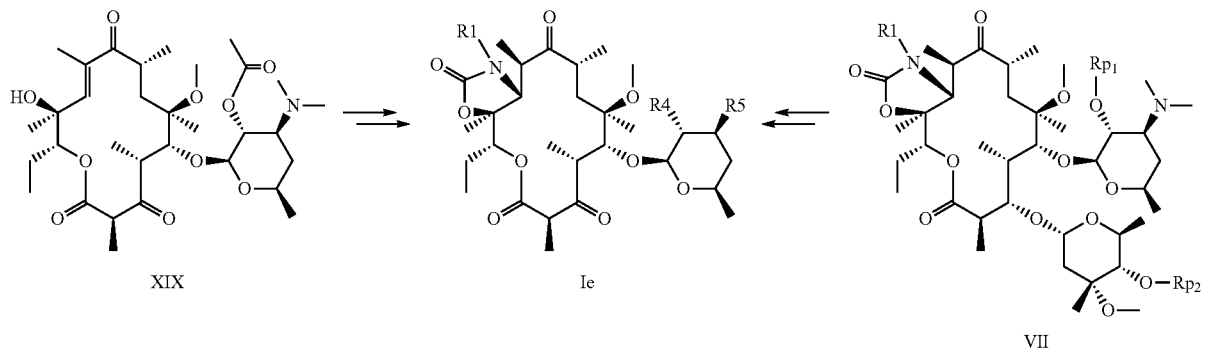

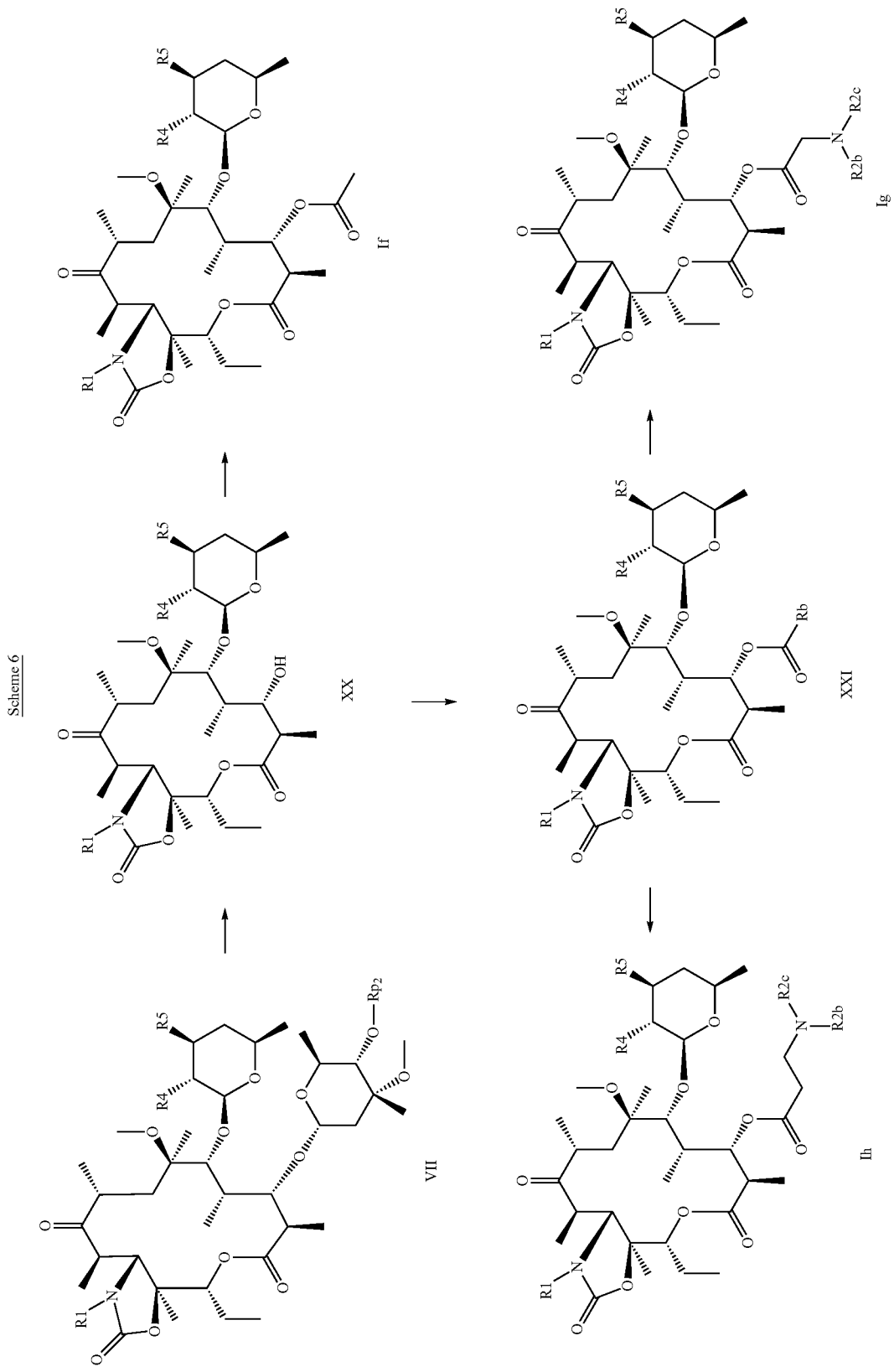

Treatment of compounds of general formula VII with acid according to well known procedures (e.g. J. Med. Chem. 1998, 41, 4080) gives compounds of formula XX. Compounds of formula XXI with Rb=—CH$_2$Cl may be obtained by reacting compounds of formula XX with 2-chloroacetyl-chloride, 2-chloroacetic acid anhydride or 2-chloroacetic acid according to methods well known for the esterification of hydroxyl groups. This compound is then reacted with an appropriate nucleophile such as for example dimethylamine or morpholine to give, after deprotection if necessary, compounds of formula Ig (scheme 6). Compounds of formula Ih are obtained in a similar way by reacting compound XX with acroyl chloride to give compound XXI wherein Rb is —CH=CH$_2$ followed by reaction with an appropriate nucleophile such as for example, dimethylamine or morpholine to give, after deprotection if necessary, compounds of formula Ih. Compounds of formula If are prepared from compounds XX by reaction with acetic anhydride.

The deprotection of intermediates to give compounds of general formula I are done according to standard procedures described for example in T. W. Green et al., Protective Groups in Organic Synthesis, John Wiley & Sons, 1999. In cases where Rp1 and Rp2 are acyl protecting groups such as acetyl and benzoyl the protecting groups are removed by stirring in methanol at 0° to 60° or by treatment of the compound with DBU in refluxing methanol for 3 to 12 hours (J. Antibiotics, 2001, 54(8), 664) or by treatment with guanidine/guanidinium nitrate in methanol/dichloromethane (Tetrahedron Letters 1997, 38(9), 1627) or with potassium carbonate in methanol or with a mixture of MeONa in methanol, preferably with DBU in refluxing methanol for 5 to 7 hours.

Modifications at position 3 of the macrolactone ring (i.e. R2-R3) and at positions 2' and 3' of the sugar moiety (i.e. R4-R5) as described in general terms in schemes 2-6 can be introduced at any suitable stage in the course of the synthesis of compounds of general formula I as outlined in scheme 1. For example substituents R5b and/or R5c can be introduced as outlined in scheme 2 starting from compound of formula VII or for example starting from compound of formula V or starting from clarithromycin. The appropriate time point for such modifications depends on the nature of the conditions applied as it is well known to any person skilled in the art and might require protection of certain functional groups with a suitable protecting group and subsequent deprotection according to standard procedures described in T. W. Green et al., Protective Groups in Organic Synthesis, John Wiley & Sons, 1999.

It is understood that individual modifications described in the schemes 1-6 can be performed sequentially with the same molecule to give compounds of general formula I i.e. modifications in position 3 of the macrolactone ring as described for example in scheme 5 can be combined with a modification of the sugar moiety as described for example in scheme 2. To avoid interference with functional groups a person skilled in the art will carry out the reactions in an appropriate order and protect and subsequently deprotect functional groups if necessary.

It is further understood that R1 in compounds of formula I, and of intermediates like those mentioned above can be further modified. For example an ester group can be hydrolyzed and the resulting acid can be coupled with an amine to form a amide according to methods well known in the art.

EXAMPLES

The following examples are given to further illustrate the invention and are not to be construed as in any way limiting the scope of the present invention.

| Example | Structure |
|---------|-----------|
| 1 | 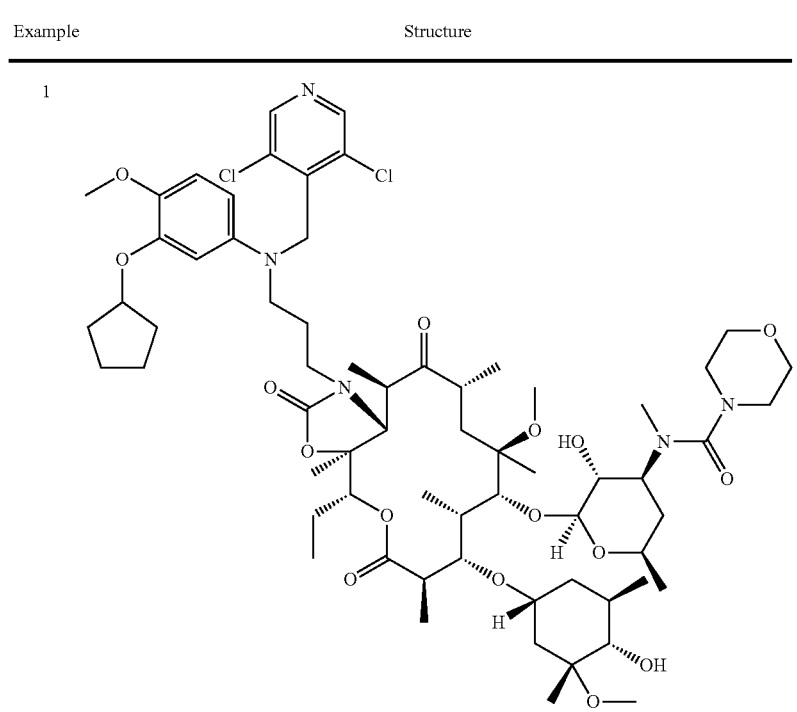 |

| Example | Structure |
|---|---|
| 2 | 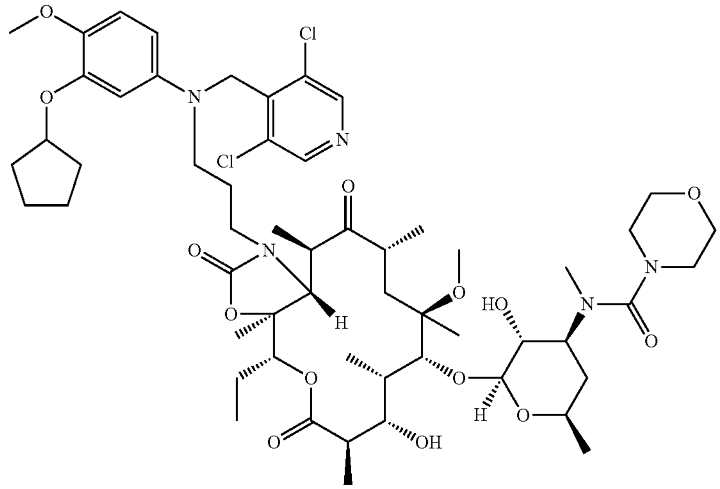 [SMILES: CC[C@H]1OC(=O)[C@H](C)[C@@H](O)[C@H](C)[C@@H](O[C@@H]2O[C@H](C)C[C@H](N(C)C(=O)N3CCOCC3)[C@H]2O)[C@](C)(OC)C[C@@H](C)C(=O)[C@H](C)[C@H]2N(CCCN(Cc3c(Cl)cncc3Cl)c3ccc(OC)c(OC4CCCC4)c3)C(=O)O[C@]12C] |
| 3 | 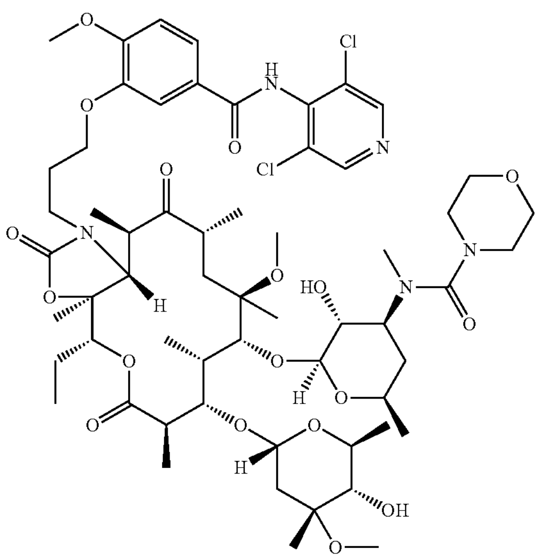 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)N3CCOCC3)[C@H]2O)[C@](C)(OC)C[C@@H](C)C(=O)[C@H](C)[C@H]2N(CCCOc3cc(C(=O)Nc4c(Cl)cncc4Cl)ccc3OC)C(=O)O[C@]12C] |
| 4 | 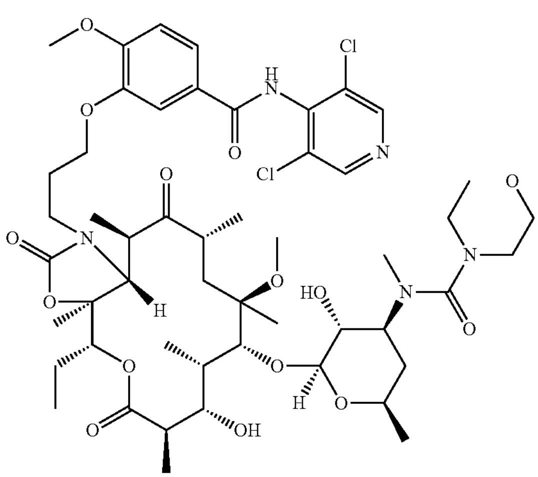 [SMILES: CC[C@H]1OC(=O)[C@H](C)[C@@H](O)[C@H](C)[C@@H](O[C@@H]2O[C@H](C)C[C@H](N(C)C(=O)N(CC)CCO)[C@H]2O)[C@](C)(OC)C[C@@H](C)C(=O)[C@H](C)[C@H]2N(CCCOc3cc(C(=O)Nc4c(Cl)cncc4Cl)ccc3OC)C(=O)O[C@]12C] |

| Example | Structure |
|---|---|
| 5 | 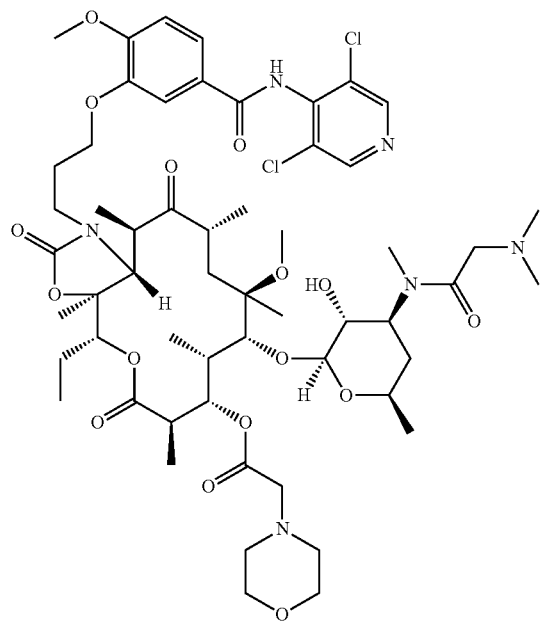 [SMILES: CC[C@H]1OC(=O)[C@H](C)[C@@H](OC(=O)CN2CCOCC2)[C@H](C)[C@@H](O[C@@H]2O[C@H](C)C[C@H](N(C)C(=O)CN(C)C)[C@H]2O)[C@](C)(OC)C[C@@H](C)C(=O)[C@H](C)[C@H]2N(CCCOc3cc(C(=O)Nc4c(Cl)cncc4Cl)ccc3OC)C(=O)O[C@]12C] |

General remarks: Analytical HPLC: System Aa: column: Bischoff Prontosil 120-3-C18 SH 3 μm, 75×4.6 mm; flow: 1.2 mL/min; detection: ELSD, UV; mobile phase A: water+3% acetonitrile+0.1% TFA; mobile phase B: acetonitrile+0.1% TFA; gradient: 0-2 min constant 5% B; 2-5 min linear from 5% to 30% B; 5-18 min linear from 30% to 55% B; 18-23.5 min linear from 55% to 95% B; 23.5-35 min 95% B. System Ba: column: SunFire C18, 3.5 μm, 150×4.6 mm; flow: 1.0 mL/min; detection: 254 nm; mobile phase A: water+0.1% TFA; mobile phase B: acetonitrile+0.1% TFA; gradient: 0-2 min constant 20% B; 2-5 min linear from 20% to 60% B; 5-20 min linear from 60% to 90% B; 20-30 min linear from 90% to 95% B. System Ca: column: SunFire C18, 5 μm, 250×4.6 mm; flow: 1.0 mL/min; detection: 254 nm; mobile phase A: water+0.1% TFA; mobile phase B: acetonitrile+0.1% TFA; gradient: 0-5 min linear from 20% to 60% B; 5-20 min linear from 60% to 90% B; 20-30 min linear from 90% to 95% B. System Da: column: SunFire C18, 5 μm, 250×4.6 mm; flow: 1.0 mL/min; detection: 254 nm; mobile phase A: water+0.1% TFA; mobile phase B: acetonitrile+0.1% TFA; gradient: 0-2 min 20% B; 2-5 min linear from 20% to 42% B; 5-20 min linear from 42% to 80% B; 20-30 min linear from 80% to 95% B. System Ea: column: Prontosil 120-3-C18 ace-EPS 3 μm, 150×4.6 mm; flow: 1.0 mL/min; detection: 254 nm; mobile phase A: water+0.1% TFA; mobile phase B: acetonitrile+0.1% TFA; gradient: 0-2 min constant 20% B; 2-5 min linear from 20% to 42% B; 5-20 min linear from 42% to 80% B; 20-30 min linear from 80% to 95% B. System Fa: column: Prontosil 120-3-C18 SH 3 nm, 150×4.6 mm; flow: 1.0 mL/min; detection: ELSD, 254 nm; mobile phase A: water+0.1% TFA; mobile phase B: acetonitrile+0.1% TFA; gradient: 0-5 min constant 10% B; 5-20 min linear from 10% to 58% B; 20-30 min linear from 58% to 95% B.

Abbreviations: HPLC for high performance liquid chromatography; DMSO for dimethylsulphoxide; DBU for diazabicycloundecane; DCM for dichloromethane; DMF for dimethylformamide; THF for tetrahydrofurane, MS for mass spectrometry; NMR for nuclear magnetic resonance; ESI for electrospray ionization.

Example 1

Preparation of I-1, compound of formula I where R1 is 3-[(3-cyclopentyloxy-4-methoxy-phenyl)-(3,5-dichloropyridin-4-yl-methyl)-amino]propyl, R2 is O-cladinosyl, R3 is hydrogen, R4 is hydroxyl and R5 is methyl-(morpholine-4-carbonyl)-amino A] Preparation of Compound 1-A

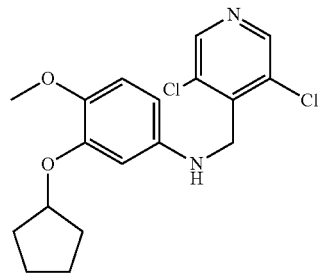 [SMILES: COc1ccc(NCc2c(Cl)cncc2Cl)cc1OC1CCCC1]

1.408 g (6.48 mmol) of 3-cyclopentyloxy-4-methoxy-phenylamine (Garcia et al., JOC, 2005, 70, p 1050) is dissolved in 20 ml toluene and 1.197 g (6.6 mmol) 3,5-dichloro-4-pyridinecarboxaldehyde, 3.6 ml (25.9 mmol) triethylamine and 1.85 ml (32.4 mmol) acetic acid are added. The mixture is stirred at 25° C. for 2 hours and then 1.629 g (25.9 mmol) NaBH$_3$CN are added and the mixture is stirred for at 25° C. for one hour. The solvent is evaporated and the crude product is purified by flash chromatography on silica gel (petroleum ether/ethyl acetate 15:1) to give 1.98 g (82%) of the desired product as a light yellow solid.

$^1$H NMR (DMSO-d6): 8.61 (s, 2H); 6.70 (d, 1H); 6.30 (d, 1H); 6.15 (dd, 1H); 5.55 (t, 1H); 4.65 (m, 1H); 4.36 (d, 2H); 3.59 (s, 3H); 1.77-1.81 (m, 2H); 1.64-1.67 (m, 4H); 1.53-1.56 (m, 2H).

B] Preparation of Compound 1-B

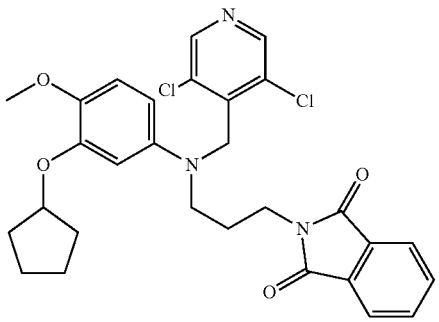 [SMILES: COc1ccc(N(CCCN2C(=O)c3ccccc3C2=O)Cc2c(Cl)cncc2Cl)cc1OC1CCCC1]

0.38 g (0.99 mmol) of compound 1-A is dissolved in 15 ml methanol and 0.26 g (1.28 mmol) of 3-(1,3-dioxo-1,3-dihydroisoindol-2-yl)-propionaldehyde, 0.1 ml acetic acid and 0.125 g (1.98 mmol) of NaBH$_3$CN are added to the solution. The mixture is stirred at 28° C. for 3.5 hours and the solvent is subsequently evaporated. The crude product is purified by column chromatography on silica gel (petroleum ether(ethyl acetate 10:1→5:1) to give 380 mg (65%) of the desired product as a light yellow solid.

C] Preparation of Compound 1-C

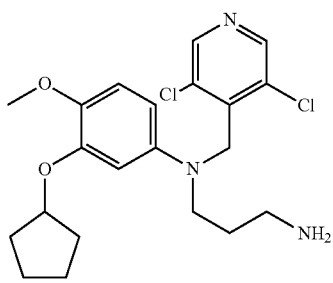 [SMILES: COc1ccc(N(CCCN)Cc2c(Cl)cncc2Cl)cc1OC1CCCC1]

0.38 g (0.69 mmol) of compound 1-B is dissolved in 20 ml ethanol and 1 ml of a hydrazine hydrate solution (85%) is added to the solution. The reaction mixture is stirred at 70° C. until no starting material remained (~1.5 hours). The precipitate that formed during the reaction is filtered off and the filtrate is concentrated under reduced pressure to afford the crude product which is purified by column chromatography on silica gel (DCM:MeOH 50:1→20:1) to give 0.23 g (79%) of the desired product as a yellow oil.

$^1$H NMR (CDCl$_3$): 8.43 (s, 2H); 6.74 (d, 1H); 6.52 (d, 1H); 6.49 (dd, 1H); 4.67 (m, 1H); 4.41 (s, 2H); 3.77 (s, 3H); 3.13 (t, 2H); 2.63 (m, 2H); 1.52-1.86 (m, 10H).

D] Preparation of Compound 1-D (Compound of Formula V where Rp1 and Rp2 are Acetyl)

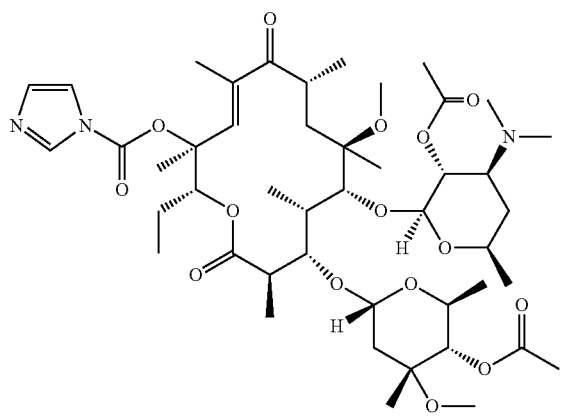 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](N(C)C)[C@H]2OC(C)=O)[C@](C)(OC)C[C@@H](C)C(=O)/C(C)=C/[C@]1(C)OC(=O)n1ccnc1]

1.0 g (24.6 mmol) of sodium hydride (60% in oil) is dissolved in 100 ml of DMF. The mixture is cooled to −10° C. and 10 g (12.3 mmol) of compound of formula IV where Rp1 and Rp2 are acetyl (WO2008017696, example 1) is added. To this mixture a solution of 6.06 g (36.9 mmol) carbonyldiimidazole (CDI) in 50 ml of DMF is added. The mixture is stirred at −10° C. for one hour and 150 ml of water is added keeping the temperature of the mixture at 0° C. The solids are filtered off and the filter cake is washed with cold water and subsequently dissolved in diethyl ether. The solution is dried over MgSO$_4$ and concentrated under reduced pressure.

The crude product (9.99 g) is purified by column chromatography on silica gel (DCM:MeOH 40:1) to give 5.56 g (56%) of the desired product as a white solid.

MS (ESI): 908.3 ([MH]$^+$)

Ret. Time (system Aa): 14.8 min.

E] Preparation of Compound 1-E

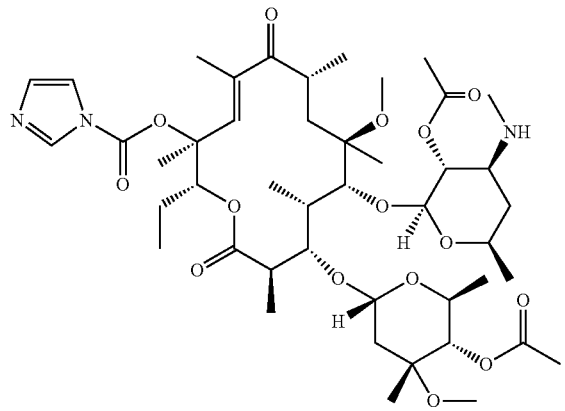

2.0 g (2.2 mmol) of compound 1-D is dissolved in 40 ml of methanol and 2 ml of water and 0.92 g of sodium acetate are added. The mixture is stirred for 10 minutes and 1.8 g (7.09 mmol) of iodine are added. The dark mixture is stirred for 1 hour at 25-30° C. The reaction mixture is quenched with a saturated aqueous solution of Na$_2$S$_2$O$_3$. The solvent is removed in vacuo and the residue is taken up in DCM. The organic layer is washed with water and with brine, dried over Na$_2$SO$_4$, filtered and concentrated under reduced pressure to give the crude product. The crude product is combined with the product from a second batch (prepared from 0.2 g of 1-D) and is purified by flash chromatography on silica gel (DCM/MeOH 200:1→60:1) to give 1.04 g (48%) of a light yellow foam.

F] Preparation of Compound 1-F

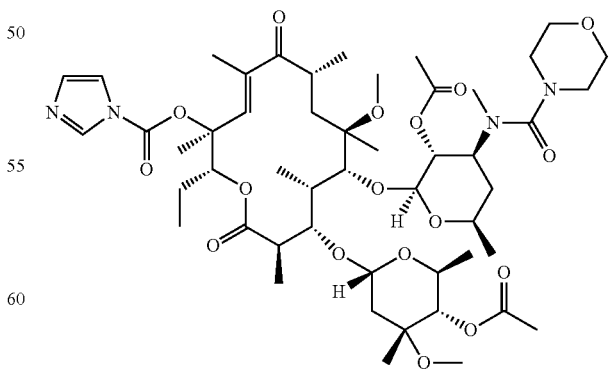

To a solution of 0.46 g (0.51 mmol) of compound 1-E in 20 ml dry THF under an atmosphere of nitrogen is added 0.2 ml diisopropyl-ethylamine. The mixture is stirred at room temperature for 10 minutes and 79 mg (0.51 mmol) of morpholino-4-carbonyl chloride is added. The reaction mixture is stirred at room temperature for 16 hours and the solvent is subsequently removed under reduced pressure and the residue is taken up in DCM. The organic layer is washed with water and with brine, dried over Na$_2$SO$_4$, filtered and concentrated under reduced pressure. The crude product is purified by flash chromatography on silica gel (DCM/MeOH 80:1) to give 370 mg (64%) of the desired product as a white foam.

G] Preparation of Compound 1-G

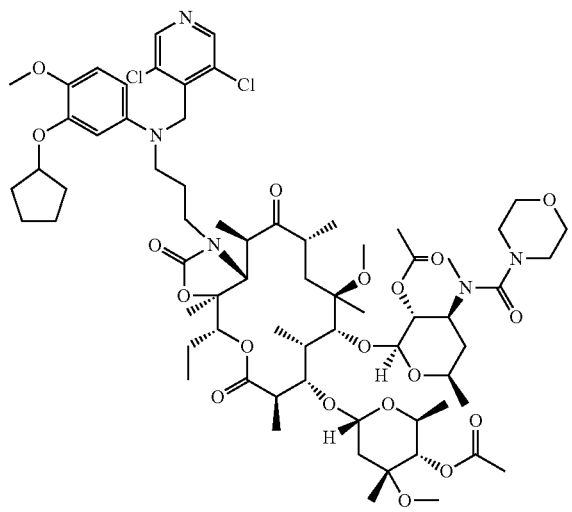 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](N(C)C(=O)N3CCOCC3)[C@H]2OC(C)=O)[C@](C)(OC)C[C@@H](C)C(=O)[C@H](C)[C@H]2N(CCCN(Cc3c(Cl)cncc3Cl)c3ccc(OC)c(OC4CCCC4)c3)C(=O)O[C@]12C]

300 mg (0.3 mmol) of compound 1-F are dissolved in 10 ml DMF and 126 mg (0.3 mmol) of compound I-C and 136 mg (0.89 mmol) DBU is added. The mixture is stirred at 60° C. for 4 days and the solvent is evaporated. The residue is taken up in DCM and the organic layer is washed with water and with brine, dried over Na$_2$SO$_4$, filtered and concentrated under reduced pressure. The crude product is purified by flash chromatography on silica gel (DCM/MeOH 120:1→60:1) and preparative HPLC to give 110 mg (27%) of the desired product as a light yellow foam.

MS (ESI): 1362.6, 1364.6 ([MH]$^+$)

H] Preparation of Compound I-1

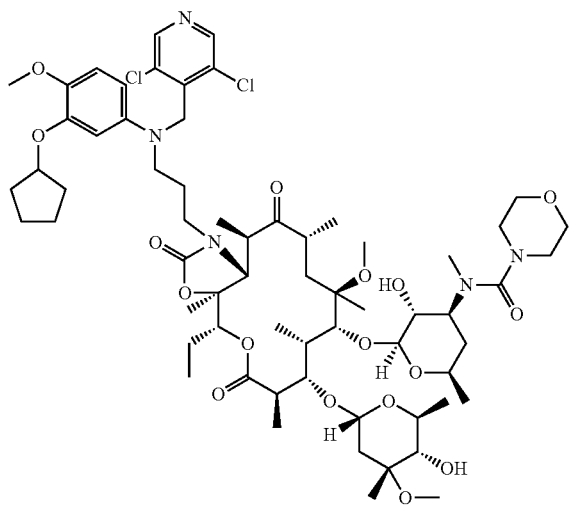 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)N3CCOCC3)[C@H]2O)[C@](C)(OC)C[C@@H](C)C(=O)[C@H](C)[C@H]2N(CCCN(Cc3c(Cl)cncc3Cl)c3ccc(OC)c(OC4CCCC4)c3)C(=O)O[C@]12C]

350 mg (0.26 mmol) of compound 1-G is dissolved in 15 ml methanol and 380 mg (2.5 mmol) DBU is added. The mixture is stirred at 65° C. for 60 hours. The solvent is removed under reduced pressure and the residue is taken up in 100 ml of DCM. The organic layer is washed twice with water and with brine, dried over Na$_2$SO$_4$, filtered and concentrated in vacuo. The crude product is combined with the product from a second batch (prepared from 0.11 g of I-G) and is purified by preparative HPLC (column: Phenomenex Gemini C18, 110A, 5 μm, 150×21.2 mm; flow: 12 mL/min; detection: 254 nm; mobile phase A: water+0.05% ammonia; mobile phase B: acetonitrile; gradient: linear from 70 to 90% acetonitrile in 10 min; 100% acetonitrile for 5 minutes) to give 60 mg of the desired product as a light yellow solid.

MS (ESI): 1278.5, 1280.6 [MH]$^+$

Ret. Time (system Ba): 19.4 min.

Example 2

Preparation of I-2. Compound of formula I where R1 is 3-[(3-cyclopentyloxy-4-methoxy-phenyl)-(3,5-dichloropyridin-4-yl-methyl)-amino]propyl, R2 is OH, R3 is hydrogen, R4 is hydroxyl and R5 is methyl-(morpholine-4-carbonyl)-amino A] Preparation of Compound I-2

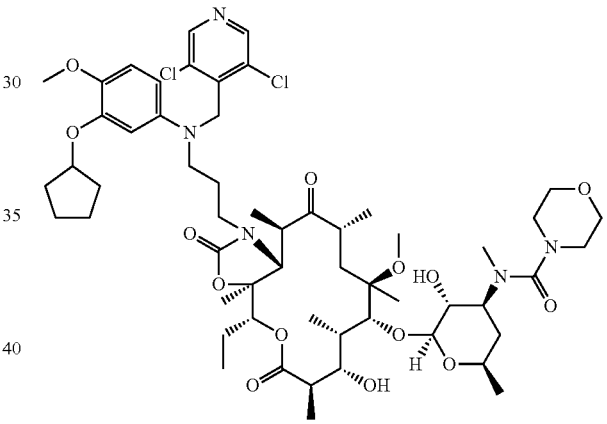

235 mg (0.18 mmol) of compound I-1 is dissolved in 20 ml of CH$_3$CN and 10 ml of 1N aqueous HCl solution is added. The mixture is stirred at 27° C. for 5 hours and then treated with 5% aqueous NaHCO$_3$ solution to adjust pH=7-8. The solvent is removed under reduced pressure and the residue is taken up in 50 ml of DCM. The organic layer is washed twice with water and with brine, dried over Na$_2$SO$_4$, filtered and concentrated in vacuo. The crude product is purified by flash chromatography on silica gel (DCM/MeOH 100:1→40:1) and preparative HPLC (column: XBridge Prep C18 OBD, 5 μm, 150×19 mm; flow: 10 ml/min; detection: 254 nm; mobile phase A: water+0.05% ammonia; mobile phase B: acetonitrile; gradient: linear from 70 to 90% acetonitrile in 13 min; 100% acetonitrile for 3 minutes) to give 70 mg (34%) of the desired product as a light yellow solid.

$^1$H NMR (CDCl$_3$, diagnostic signals only): 0.80 (t, 3H), 1.05 (d, 3H), 1.09 (d, 3H), 1.11 (d, 3H), 1.25 (d, 3H), 1.27 (d, 3H), 1.33 (s, 3H), 1.41 (s, 3H), 2.50-2.61 (m, 1H), 2.62-2.72 (m, 1H), 2.78 (s, 3H), 2.79 (s, 3H), 2.95-3.05 (m, 1H), 3.77 (s, 3H), 3.87-3.96 (m, 1H), 4.18 (m, 1H(OH)), 4.40 (d, 1H), 4.49 (s, 2H), 4.71 (m, 1H), 4.97 (dd, 1H), 6.45-6.52 (m, 2H), 6.69-6.74 (m, 1H), 8.41 (s, 2H)

MS (ESI): 1120.5, 1122.5 [MH]$^+$

Ret. Time (system Ca): 18.4 min

Example 3

Preparation of I-3, compound of formula I where R1 is 3-[5-(3,5-dichloropyridine-4-yl-aminocarbonyl)-2-methoxy-phenoxy]propyl, R2 is O-cladinosyl, R3 is hydrogen, R4 is hydroxyl and R5 is methyl-(morpholine-4-carbonyl)-amino A] Preparation of Compound 3-A

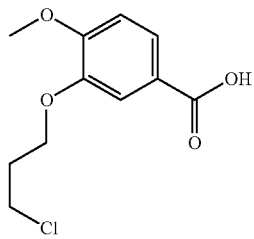 [SMILES: COc1ccc(C(=O)O)cc1OCCCCl]

200 mg (1.19 mmol) of isovanillic acid are dissolved in 10 ml DMF and 493 mg (3.57 mmol) potassium carbonate and 0.35 ml (3.57 mmol) 1-bromo-3-chloropropane are added. The mixture is heated to 50° C. for 4 hours. Subsequently 20 ml of water is added and the aqueous layer is extracted twice with 20 ml of ethyl acetate. The organic layers are combined and the solvent is evaporated under reduced pressure. The residue is dissolved in 20 ml THF and 20 ml methanol and 20 ml of 4N aqueous NaOH is added. The reaction mixture is stirred for 2 hours at room temperature and the organic solvents are evaporated. The aqueous phase is adjusted to pH=7 with concentrated aqueous HCl leading to precipitation of the product which is isolated by filtration and washed with water to give 100 mg of the desired product as white solid.

$^1$H NMR (DMSO-d6): 2.13-2.19 (m, 2H), 3.76-3.79 (m, 2H), 3.82 (s, 3H), 4.08-4.11 (m, 2H), 7.03 (d, 1H), 7.44 (s, 1H), 7.56 (d, 1H), 12.7 (bs, 1H)

B] Preparation of Compound 3-B

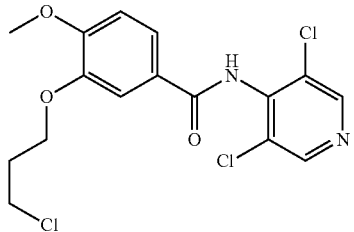 [SMILES: COc1ccc(C(=O)Nc2c(Cl)cncc2Cl)cc1OCCCCl]

292 mg (6.99 mmol) sodium hydride (55-60% dispersion in mineral oil) are suspended in 10 ml DMF and 1.266 g (7.77 mmol) of 4-amino-3,5-dichloropyridine is added. The mixture is stirred for 3 hours at 30° C. to give "solution A".

500 mg (2.05 mmol) of compound 3-A, 932 mg (2.45 mmol) of HATU and 317 mg (2.45 mmol) of ethyl-diisopropyl-amine are dissolved in 10 ml DMF and the resulting solution is stirred at 30° C. for 60 minutes. Solution A (see above) is added dropwise at 0-10° C. and the mixture is stirred at this temperature for 15 minutes. The pH of the mixture is adjusted to 6 by addition of aqueous HCl and DMF is evaporated under reduced pressure. The residue is dissolved in 50 ml ethyl acetate and the organic layer is washed twice with 50 ml 0.5 N aqueous HCl, with 50 ml water and twice with 50 ml brine, dried over Na$_2$SO$_4$ and concentrated in vacuo to give the crude product. The crude product is purified by flash chromatography on silica gel (petroleum ether/ethyl acetate 3:1) to give 360 mg of the desired product as white solid.

$^1$H NMR (DMSO-d6): 2.16-2.20 (m, 2H), 3.78-3.81 (m, 2H), 3.84 (s, 3H), 4.12-4.15 (m, 2H), 7.12 (d, 1H), 7.59 (s, 1H), 7.67 (d, 1H), 8.72 (s, 2H), 10.40 (bs, 1H)

C] Preparation of Compound 3-C

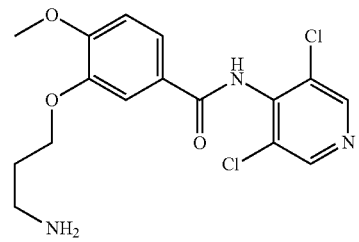 [SMILES: COc1ccc(C(=O)Nc2c(Cl)cncc2Cl)cc1OCCCN]

300 mg (0.77 mmol) of compound 3-B is dissolved in an autoclave in 60 ml of dry THF and 14 g of liquid ammonia are added at −70° C. The mixture is stirred at 90° C. for 1 day. The solvent is removed under reduced pressure and the residue is purified by flash chromatography on silica gel (DCM/MeOH 5:1) to give 230 mg (81%) of the desired product as a light brown solid.

$^1$H NMR (CD$_3$OD): 2.17-2.23 (m, 2H), 3.21-3.24 (m, 2H), 3.96 (s, 3H), 4.24-4.27 (m, 2H), 7.15 (d, 1H), 7.63 (d, 1H), 7.74 (dd, 1H), 8.63 (s, 2H)

MS (ESI): 370.0, 372.0 [MH]$^+$

D] Preparation of Compound 3-D

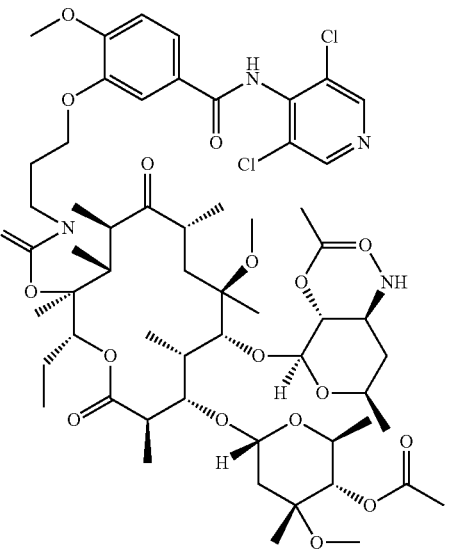

1000 mg (1.12 mmol) of compound 1-E are dissolved in 15 ml dry DMF and 456 mg (1.23 mmol) of compound 3-C and 550 mg (3.61 mmol) DBU are added. The mixture is stirred at 60-65° C. for 22 hours and the solvent is evaporated. The residue is taken up in DCM and the organic layer is washed twice with water and with brine, dried over Na$_2$SO$_4$, filtered and concentrated under reduced pressure. The crude product is purified by flash chromatography on silica gel (DCM/MeOH 200:1→70:1) to give 450 mg (32%) of the desired product as a white solid.

MS (ESI): 1195.4 [MH]$^+$

E] Preparation of Compound 3-E

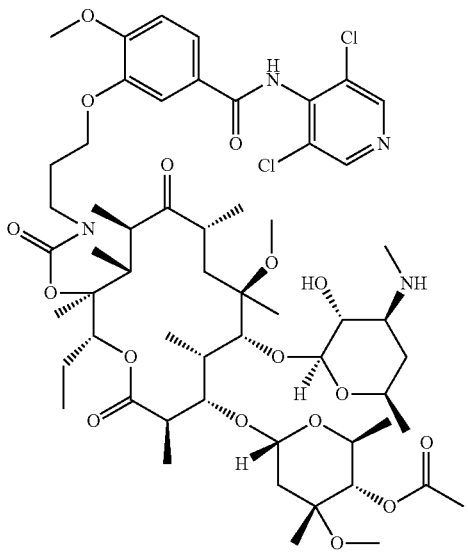 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](NC)[C@H]2O)[C@](C)(OC)C[C@@H](C)C(=O)[C@H](C)[C@@H](C)[C@]1(C)OC(=O)NCCCOc1cc(C(=O)Nc2c(Cl)cncc2Cl)ccc1OC]

1.53 g (1.28 mmol) of compound 3-D are dissolved in 40 ml methanol and 1.5 g DBU are added. The mixture is stirred at 60-65° C. for 48 hours and 0.5 g K$_2$CO$_3$ are added and the mixture is stirred at 60-65° C. for 72 hours to give a mixture of compound 3-D and the target compound. The solvent is evaporated and the residue is taken up in DCM and the organic layer is washed with water and with brine, dried over Na$_2$SO$_4$, filtered and concentrated under reduced pressure. The crude product is purified by flash chromatography on silica gel (DCM/MeOH 100:1→10:1) to give 132 mg (9%) of the desired product as light yellow foam.

MS (ESI): 1111.2, 1113.3 [MH]$^+$

F] Preparation of Compound I-3

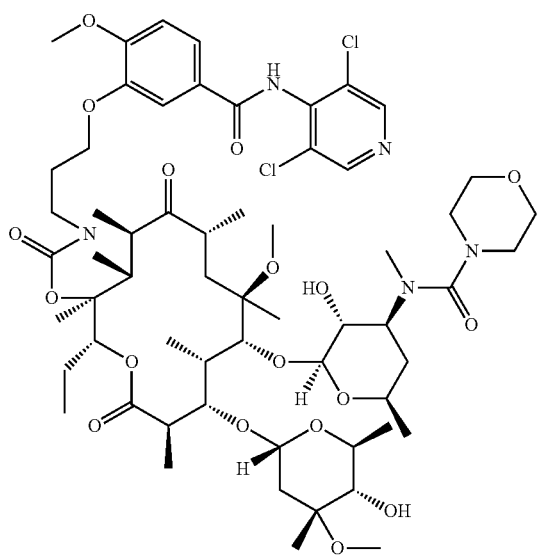 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)N3CCOCC3)[C@H]2O)[C@](C)(OC)C[C@@H](C)C(=O)[C@H](C)[C@@H](C)[C@]1(C)OC(=O)NCCCOc1cc(C(=O)Nc2c(Cl)cncc2Cl)ccc1OC]

132 mg (0.12 mmol) of compound 3-E are dissolved in 10 ml dry THF under an atmosphere of nitrogen and 80 mg (0.62 mmol) diisopropyl-ethylamine and 53 mg (0.35 mmol) of morpholino-4-carbonyl chloride are added. The mixture is stirred at 15° C. for 20 hours and the solvent is subsequently removed under reduced pressure and the residue is taken up in DCM. The organic layer is washed with water, dried over Na$_2$SO$_4$, filtered and concentrated under reduced pressure. The crude product is purified by flash chromatography on silica gel (DCM/MeOH 120:1→70:1) and subsequently by preparative HPLC (column: Phenomenex Gemini C18 110A, 5 μm, 150×21.2 mm; flow: 13 ml/min; detection: 254 nm; mobile phase A: water+0.1% ammonia; mobile phase B: methanol; gradient: linear from 55 to 75% methanol in 10 min; 100% methanol for 5 minutes) to give 45 mg (15%) of the desired product as white solid.

$^1$H NMR (CDCl$_3$, diagnostic signals only): 0.79 (t, 3H), 0.98-1.05 (m, 6H), 1.09 (d, 3H), 1.16 (d, 3H), 1.21 (d, 3H), 1.24 (s, 3H), 1.27 (d, 3H), 1.33 (s, 3H), 1.38 (s, 3H), 2.82 (s, 3H), 2.99 (s, 3H), 3.33 (s, 3H), 3.93 (s, 3H), 4.27-4.36 (m, 1H), 4.43 (d, 1H), 4.85 (d, 1H), 4.93 (dd, 1H), 6.97 (d, 1H), 7.67-7.78 (m, 2H), 8.54 (s, 2H), 8.84 (s, 1H)

MS (ESI): 1224.4, 1226.4 [MH]$^+$

Ret. Time (system Da): 20.1 min.

Example 4

Preparation of I-4, compound of formula I where R1 is 3-[5-(3,5-dichloropyridine-4-yl-aminocarbonyl)-2-methoxy-phenoxy]propyl, R2 is OH, R3 is hydrogen, R4 is hydroxyl and R5 is methyl-(morpholine-4-carbonyl)-amino A] Preparation of Compound I-4

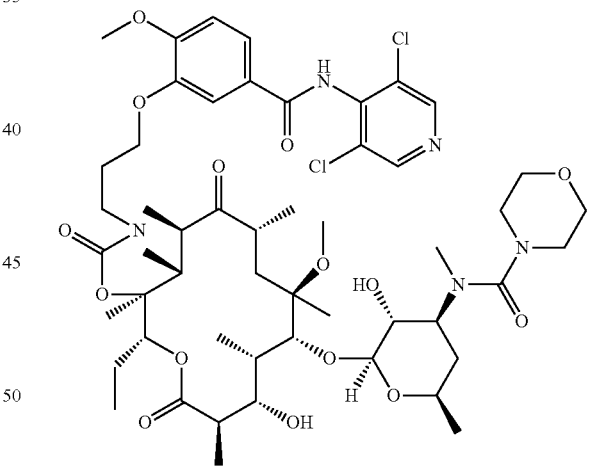

The compound I-4 is prepared following the procedure described in example 2 step A.

$^1$H NMR (CDCl$_3$, diagnostic signals only): 0.79 (t, 3H), 1.01 (d, 3H), 1.05 (d, 3H), 1.09 (d, 3H), 1.21 (d, 3H), 1.26 (d, 3H), 1.32 (s, 3H), 1.42 (s, 3H), 2.35-2.47 (m. 1H), 2.61-2.71 (m, 1H) 2.79 (s, 3H), 2.96 (s, 3H), 2.99-3.08 (m, 1H), 3.14-3.25 (m, 2H), 3.93 (s, 3H), 4.03-4.12 (m, 1H), 4.27-4.35 (m, 1H), 4.39 (d, 1H), 5.03 (dd, 1H), 6.98 (d, 1H), 7.67-7.75 (m, 2H), 8.54 (s, 2H), 8.82 (s, 1H)

MS (ESI): 1066.4, 1068.4 [MH]$^+$

Ret. Time (system Ea): 14.6 min.

Example 5

Preparation of I-5, compound of formula I where R1 is 3-[5-(3,5-dichloropyridine-4-yl-aminocarbonyl)-2-methoxy-phenoxy]propyl, R2 is 2-morpholin-4-yl-acetoxy, R3 is hydrogen, R4 is hydroxyl and R5 is (2-dimethylamino-acetyl)-methyl-amino A] Preparation of Compound 5-A

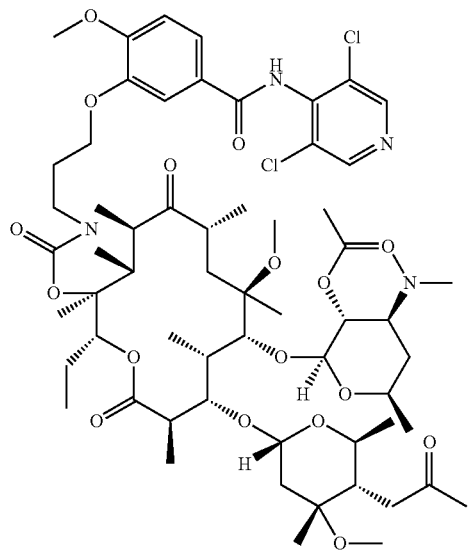

Compound 5-A is prepared from compound 1-D (example 1) and compound 3-C (example 3) following the procedure described in example 3, step D.

MS (ESI): 605.3 [(M+2H)/2]$^+$

B] Preparation of Compound 5-B

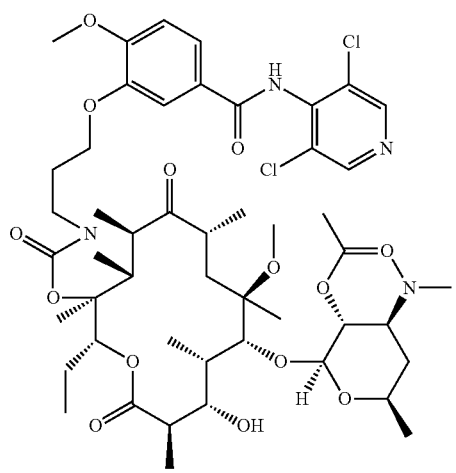

To a solution of 5.8 g of compound 5-A in 100 ml acetonitrile are slowly added 100 ml of aqueous HCl (1N) at 30° C. The resulting mixture is stirred at this temperature until no starting material remains (~12 hours). 50 ml aqueous NaHCO$_3$ (saturated solution) is added carefully to the reaction mixture. The organic solvent is removed under reduced pressure and the aqueous layer is extracted twice with 30 ml DCM. The organic layers are dried over Na$_2$SO$_4$, filtered and concentrated under reduced pressure to afford 4.0 g of the crude product as a white solid. The crude product is purified by chromatography on silica gel using DCM/MeOH (50/1) to afford 2.0 g of the desired compound as white foam.

MS (ESI): 1011.3 [MH]$^+$, 506.0 [(M+2H)/2]$^+$

C] Preparation of Compound 5-C

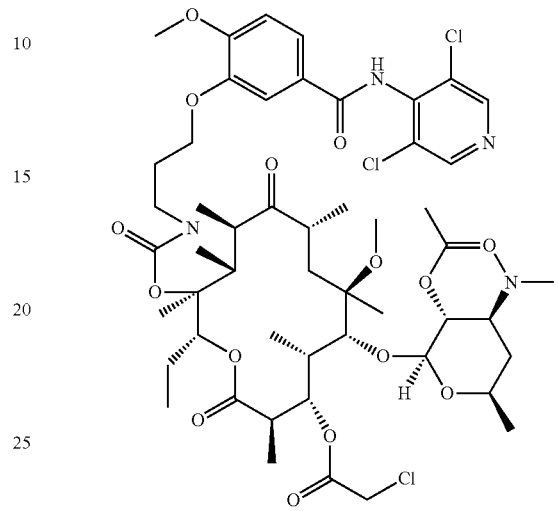

2.0 g (1.98 mmol) of compound 5-B are dissolved in 50 ml DCM and 0.74 g (4.36 mmol) chloroacetic acid anhydride and 0.48 g (3.96 mmol) DMAP are added to the mixture. The mixture is stirred at 26° C. and after 10 min 0.39 g pyridine is added. The reaction is stirred at 30° C. for one hour and subsequently poured into 50 ml water. The mixture is extracted twice with 100 ml DCM. The combined organic layers are washed with aqueous HCl (5%), water, saturated aqueous NaHCO$_3$ and brine, dried over Na$_2$SO$_4$, filtered and concentrated under reduced pressure to afford 2.2 g of the desired product as off-white solid. The crude product is used without further purification for the next step.

MS (ESI): 544.2 [(M+2H)/2]$^+$

D] Preparation of Compound 5-D

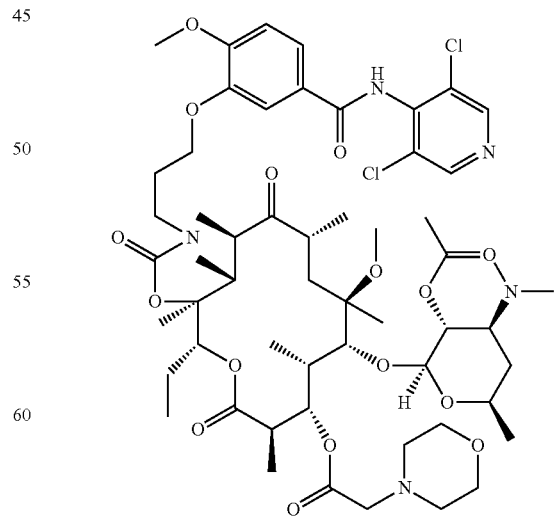

To a solution of 2.2 g (2.2 mmol) of compound 5-C in 50 ml acetonitrile are added 1.7 g (12.2 mmol) K$_2$CO$_3$, 61 mg (0.4 mmol) sodium iodide and 0.42 g (4.4 mmol) morpholine. The mixture is stirred at 50° C. for 6 hours and the solvent is removed under reduced pressure. The residue is taken up in 50 ml DCM and the organic layer is washed with water, aqueous HCl (5%), saturated aqueous NaHCO$_3$ and brine, dried over Na$_2$SO$_4$, filtered and concentrated under reduced pressure. The crude product is purified by flash chromatography on silica gel (DCM/MeOH 70:1) to give 1.2 g (52%) of the desired product as a white foam.

MS (ESI): 569.5 [(M+2H)/2]$^+$

E] Preparation of Compound 5-E

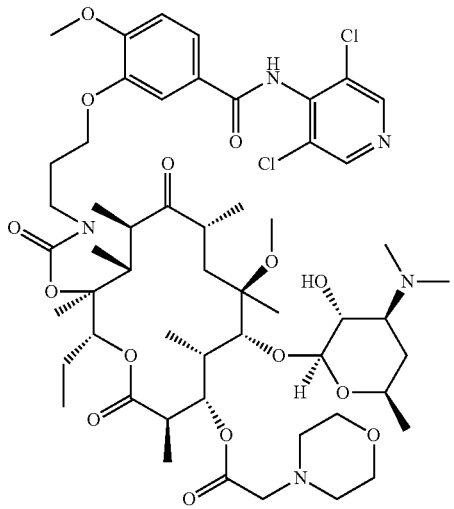 [SMILES: CC[C@H]1OC(=O)[C@H](C)[C@@H](OC(=O)CN2CCOCC2)[C@H](C)[C@@H](O[C@@H]2O[C@H](C)C[C@H](N(C)C)[C@H]2O)[C@](C)(OC)C[C@@H](C)C(=O)[C@H](C)[C@@H](C)[C@]1(C)OC(=O)NCCCOc1cc(C(=O)Nc2c(Cl)cncc2Cl)ccc1OC]

1.2 g of compound 5-D is dissolved in 50 ml methanol and stirred at 26° C. until no starting material remained (~12-18 h). The resulting mixture is used directly for the next step.

MS (ESI): 1094.3 [MH]$^+$, 547.7 [(M+2H)/2]$^+$

F] Preparation of Compound 5-F

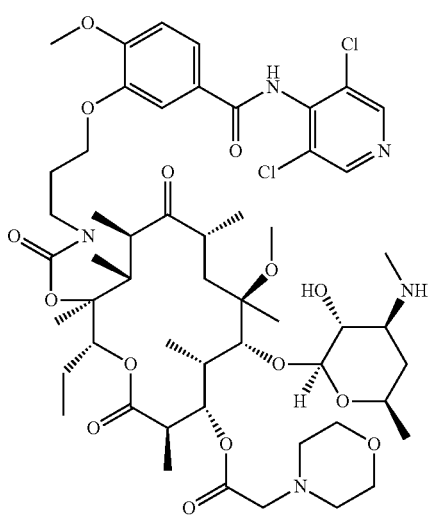 [SMILES: CC[C@H]1OC(=O)[C@H](C)[C@@H](OC(=O)CN2CCOCC2)[C@H](C)[C@@H](O[C@@H]2O[C@H](C)C[C@H](NC)[C@H]2O)[C@](C)(OC)C[C@@H](C)C(=O)[C@H](C)[C@@H](C)[C@]1(C)OC(=O)NCCCOc1cc(C(=O)Nc2c(Cl)cncc2Cl)ccc1OC]

To the solution of 1.2 g (1.1 mmol) of compound 5-E obtained in example 5 step E is added 5 ml water and 0.45 g (5.48 mmol) sodium acetate. After 5 minutes 0.56 g (2.18 mmol) iodide is added and the mixture is stirred at 60° C. until no starting material remained. The reaction mixture is quenched with a 1M aqueous solution of Na$_2$S$_2$O$_3$. The solvent is removed in vacuo and the residue is taken up in DCM. The organic layer is washed with aqueous NaHCO$_3$ (5%), water and with brine, dried over Na$_2$SO$_4$, filtered and concentrated under reduced pressure to give 1 g of the crude product as a light yellow foam.

MS (ESI): 1080.2 [MH]$^+$, 540.7 [(M+2H)/2]$^+$

G] Preparation of Compound I-5

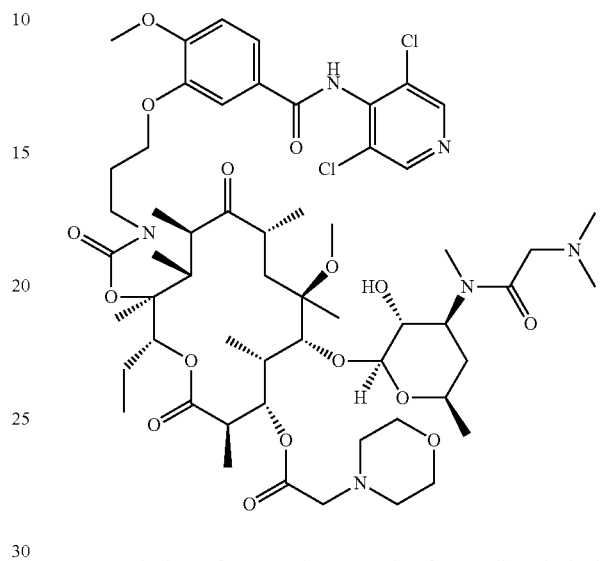

To a solution of 72 mg (0.7 mmol) of N,N-dimethyl-glycine and 93 mg (0.72 mmol) diisopropyl-ethylamine in 10 ml DMF is added 274 mg (0.72 mmol) HATU (2-(7-aza-1H-benzotriazole-1-yl)-1,1,3,3-tetramethyluronium hexafluorophosphate). The mixture is stirred for 5 minutes and 420 mg (0.39 mmol) of compound 5-F dissolved in 10 ml DMF is added. The resulting mixture is stirred for 1 hour at room temperature. The solvent is evaporated under reduced pressure and the crude product is purified by preparative HPLC (Column: XBridge Prep C18 OBD, 5 µm, 150×19 mm; flow: 15 ml/min; detection: 210 nm; mobile phase A: water+0.05% ammonia; mobile phase B: acetonitrile; gradient: linear from 40 to 70% acetonitrile in 10 min; 100% acetonitrile for 5 minutes) to give 116 mg of the desired product as a white solid.

MS (ESI): 1165.4 [MH]$^+$, 583.4 [(M+2H)/2]$^+$

Ret. Time (system Ea): 14.6 min.

Biological Activity

The compounds of the invention exhibit substantial inhibitory activity towards human phosphodiesterases (PDEs), in particular towards PDE4. The following assay is used to determine the inhibitory activity of the compounds.

Assay

PDE4 specifically hydrolyzes cAMP and releases the product AMP. The potency of PDE inhibition by said agents is determined in an in vitro enzymatic assay. The assay is commercially available (IMAP™ FP assay Molecular Devices Corp. (MDS)) and is optimized for the use of human PDE4. Fluorescently labeled cAMP is hydrolyzed by PDE4 and in a second step, binding of labeled product to a large binding partner allowed product detection by fluorescence polarization (FP) measurements.

PDE4 is partially purified from undifferentiated human monocytic cells (U-937) according to Thorpy et al. 1992 (*J. Pharmacol. Exp. Ther.* 263: 1195). Final preparations are specific for cAMP and did not hydrolyze cGMP above the detection limit of the assay. In addition, PDE4 preparations are validated by inhibition studies with PDE4-specific and unspecific PDE inhibitors.

Stock solutions of test compounds are made in DMSO and diluted in assay buffer (10 mM Tris-HCl, 10 mM $MgCl_2$, 0.1% BSA 0.05% $NaN_3$, pH 7.2) to the desired concentrations. The solutions used in the assay contained test compound in assay buffer with 2% DMSO.

10 μl of substrate (at a concentration recommended by the manufacturer) are mixed with 5 μl of appropriately diluted PDE and 5 μl of test compound solution. 5 μl of reaction buffer with 2% DMSO are used for control reactions. The final concentration of DMSO in the assay is 0.5%, which did not significantly alter the PDE activity. After incubation for 90 minutes at room temperature, 60 μl of binding reagent are added as specified by the manufacturer. Binding is allowed to proceed for 30 minutes and fluorescence polarization is measured. Dose dependence of PDE inhibition is measured by assaying dilution series of test compounds in duplicates. $IC_{50}$ values are determined from the measured activities by curve fitting.

Results:

| Example | $IC_{50}$ (PDE4) [μM] |
| --- | --- |
| 1 | 0.23 |
| 2 | 0.88 |
| 3 | 0.63 |
| 4 | 0.03 |
| 5 | 0.20 |

The invention claimed is:

1. A macrolide compound of the formula I:

wherein:
R1 is a residue —X-Q;
X is a bond or a linear group which linear group consists of hydrogen atoms and from 1 to 7 atoms selected from C, N, O and S, of which from 1 to 2 atoms can be N and one atom can be O or S, one carbon atom can appear as a CO group and the sulfur atom can appear as an $SO_2$ group and two adjacent C atoms can be present as —CH═CH— or —C≡C— and which linear group is unsubstituted or substituted;
Q is the residue -V-A1-L-A2-W;
V is an optionally substituted divalent aromatic or heterocyclic group;
W is optionally substituted aryl or heterocyclyl;
A1 and A2 are, independently of each other, either absent or a $C_1$-$C_4$alkylene group;
L is —O—, —S—, —$SO_2$—, —NH—, —CO—, —(CO)O—, —O(CO)—, —(CO)NH—, —NH(CO)—, —($SO_2$)NH—, —HN($SO_2$)—, —HN(CO)NH—, —O(CO)NH— or —NH(CO)O—;
R2 is OR2a or wherein represents the linking bond;
R2a is hydrogen, acetyl, —(C═O)$CH_2$NR2bR2c, or —(C═O)$CH_2CH_2$NR2bR2c;
R2b and R2c independently of each other, are hydrogen or C1-C6 alkyl which can be substituted or unsubstituted and wherein up to two atoms can be N, O or S and one carbon atom can appear as C═O or, taken together with the nitrogen atom to which they are linked, form a 4-7 membered-ring of which up to two atoms can be N, O or S and one carbon can appear as C═O;
R3 is hydrogen or
R2 and R3 taken together with the carbon atom to which they are linked, form a C═O group;
Z is wherein represents the linking bond;
R4 is —OR4a;
R5 is —NR5bR5c; or
R4 taken together with
R5 represent a group —O(CO)NR45-
R4a is hydrogen or C1-C6 alkyl which can be substituted or unsubstituted and wherein one or more single bonds can be replaced by double and/or triple bonds and where one carbon atom can appear as C═O and up to two atoms can be N, O or S;
R45 is hydrogen or C1-C6 alkyl;
R5b, R5c independently of one another, are hydrogen, C1-C6alkyl which can be substituted or unsubstituted, and up to two atoms of which can be N, O or S and where one carbon atom can appear as C=O, or —(C=O) heterocyclyl or, taken together with the nitrogen atom to which they are linked, form a 4-7 membered-ring of which up to two atoms can be N, O or S and one carbon can appear as C=O;

wherein alkyl groups may be substituted with one or more substituents selected from the group consisting of $C_1$-$C_4$alkoxy, $C_3$-$C_7$cycloalkyloxy or $C_3$-$C_7$cycloalkyl-$C_1$-$C_4$alkoxy, halogen, halogen substituted alkyl groups, cyano, nitro, amino, alkylamino, dialkylamino, alkylthio, mercapto, hydroxy, carbamoyl, carboxyl and oxo, and provided that R5 is not a dimethylamino group;

or a pharmaceutically acceptable salt, a N-oxide or an in vivo cleavable ester of said compound of formula (I).

2. A compound according to claim 1, wherein R4a is C1-C6alkyl or hydrogen.

3. A compound according to claim 1, wherein R5 is —NR5bR5c.

4. A compound according to claim 1, wherein R4 taken together with R5 represent a group —O(CO)NR45-.

5. A compound according to claim 1, wherein R3 is hydrogen.

6. A compound according to claim 1, wherein:
R2 is

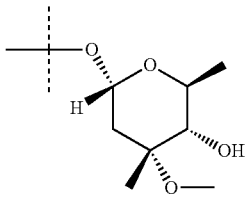

wherein

represents the linking bond.

7. A compound according to claim 1, wherein R2a is hydrogen.

8. A compound according to claim 1, wherein R2a is —(C=O)CH₂NR2bR2c or —(C=O)CH₂CH₂NR2bR2c.

9. A compound according to claim 1, wherein R2 and R3 taken together with the carbon atom to which they are linked represent a C=O group.

10. A compound according claim 1, wherein:
V is a divalent group of formula

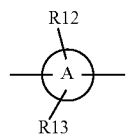

wherein:

is a phenylene ring or a x-membered saturated or unsaturated divalent heterocycloaliphatic or heteroaromatic ring containing from 1 to (x–1) carbon atoms with x being 5 to 8, and from 1 to (x–1) hetero atoms selected from the group consisting of sulfur, oxygen and nitrogen, R12 and R13 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen-substituted $C_1$-$C_4$alkoxy groups, cyano, nitro, amino, $C_1$-$C_4$alkylamino, di($C_1$-C4)alkylamino, $C_1$-$C_4$alkylthio, mercapto, hydroxy, carbamoyl, a carboxyl group, an oxo group; or aryl or heterocyclyl, which may be unsubstituted or substituted with one or more of the above identified substituents other than aryl or heterocyclyl, or when both substituents R12 and R13 are located at adjacent carbon atoms of the ring

these two substituents, taken together with said adjacent carbon atoms, can also form a 5- or 6-membered aromatic or a x-membered saturated or unsaturated heterocycloaliphatic or heteroaromatic ring containing from 2 to (x–1) carbon atoms with x being 5 to 8, and from 1 to (x–2), hetero atoms selected from the group consisting of sulfur, oxygen and nitrogen, and wherein V can have alltogether one to four substituents of the kind as defined for R12 and R13 and the free valences can be located either on one or on both rings of the group V.

11. A compound according to claim 10, wherein:
V is a divalent group of formula

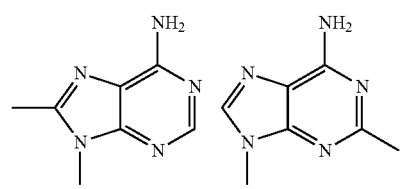

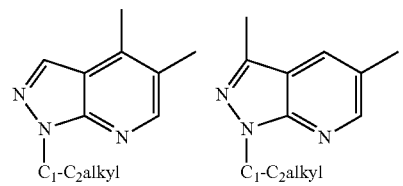

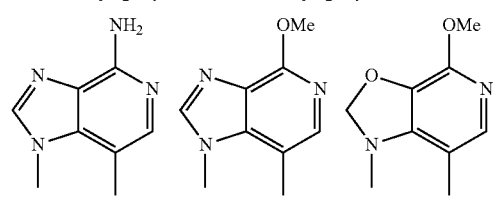

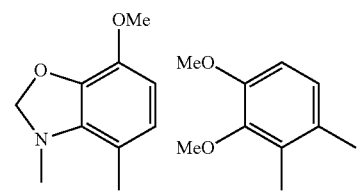

-continued

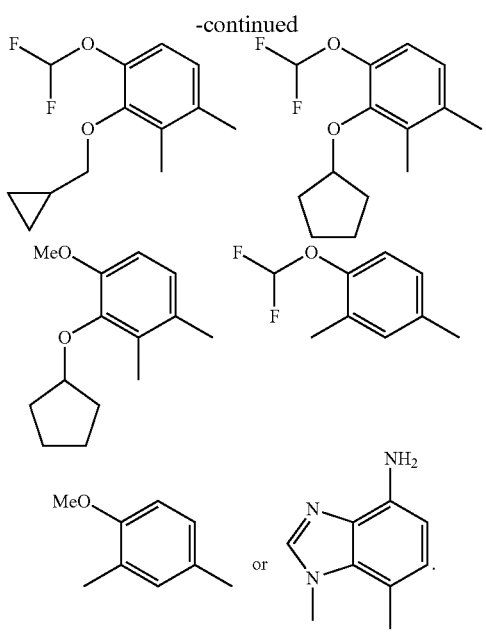

12. A compound according to claim 1, wherein W is aryl.

13. A compound according to claim 1, wherein W is a group of formula

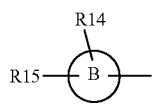

wherein

is a phenyl ring or a x-membered saturated or unsaturated monovalent heterocycloaliphatic or heteroaromatic ring containing from 1 to (x−1) carbon atoms with x being 5 to 8, and from 1 to (x−1) hetero atoms selected from the group consisting of sulfur, oxygen and nitrogen, R14 and R15 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen-substituted $C_1$-$C_4$alkoxy groups, cyano, nitro, amino, $C_1$-$C_4$alkylamino, di($C_1$-C4)alkylamino, $C_1$-$C_4$alkylthio, mercapto, hydroxy, carbamoyl, a carboxyl group, and an oxo group; or when both substituents R14 and R15 are located at adjacent carbon atoms of the ring

, these two substituents, taken together with said adjacent carbon atoms, can also form a 5- or 6-membered aromatic or a x-membered saturated or unsaturated heterocycloaliphatic or heteroaromatic ring containing from 2 to (x−1) carbon atoms with x being 5 to 8, and from 1 to (x−2), hetero atoms selected from the group consisting of sulfur, oxygen and nitrogen, wherein W can have altogether one to four substituents of the kind as defined for R14 and R15 and the free valence can be located on either ring of the group W.

14. A compound according to claim 13, wherein:
W is a group of one of the formulae

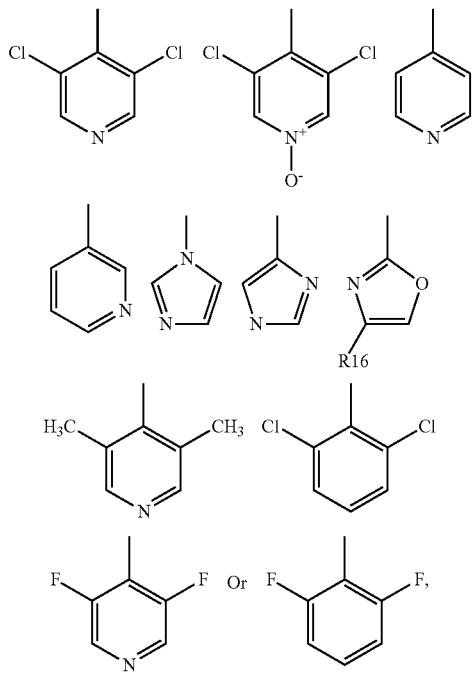

wherein R16 is hydrogen or $C_1$-$C_4$alkyl.

15. A compound according to claim 1, wherein W is a group of one of the formulae:

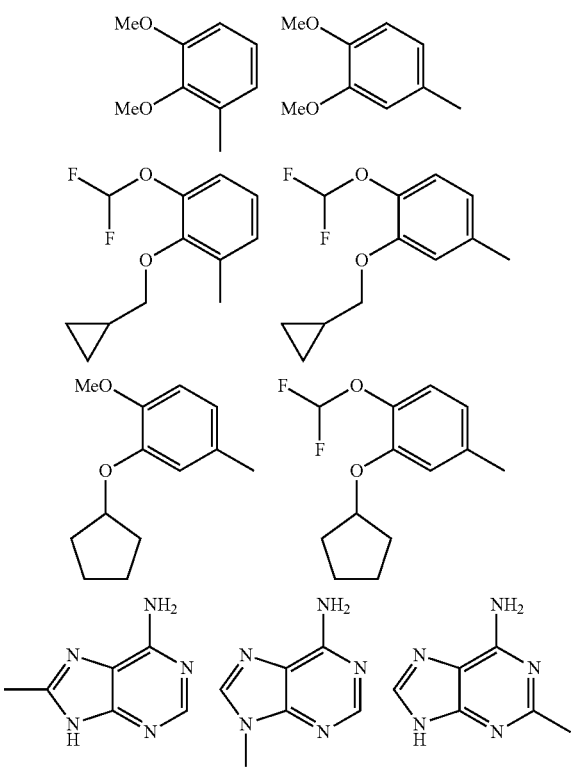

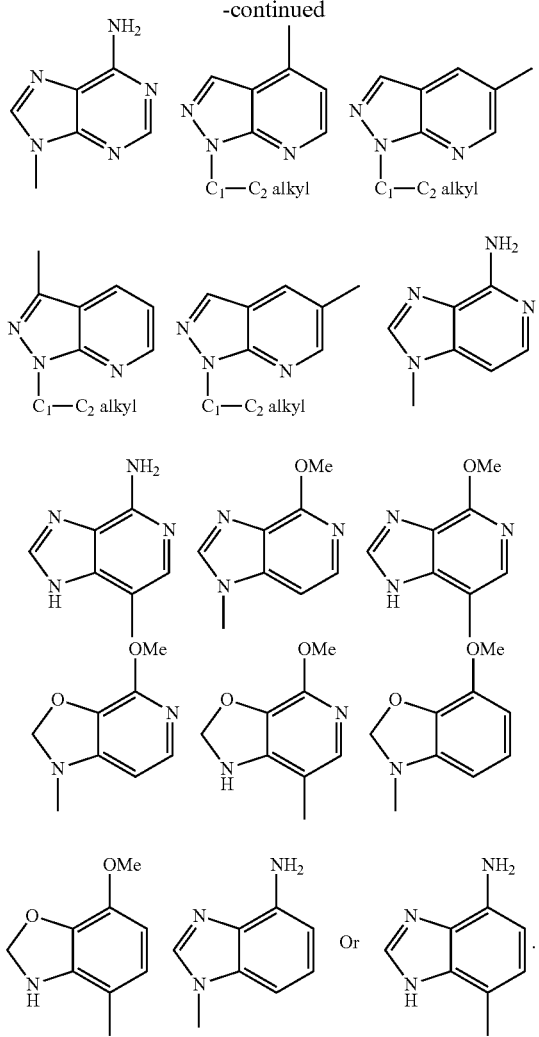

16. A compound according to claim 1, wherein A1, A2 are independently of each other either absent or a $C_1$-$C_2$alkylene group; and L is —NH—, —(CO)NH— or —NH(CO)— or is absent.

17. A compound according to claim 16, wherein:
A1, A2 are independently of each other either absent or a $C_1$-$C_2$alkylene group;
L is —NH—, —(CO)NH— or —NH(CO)—;
V is a divalent group of formula

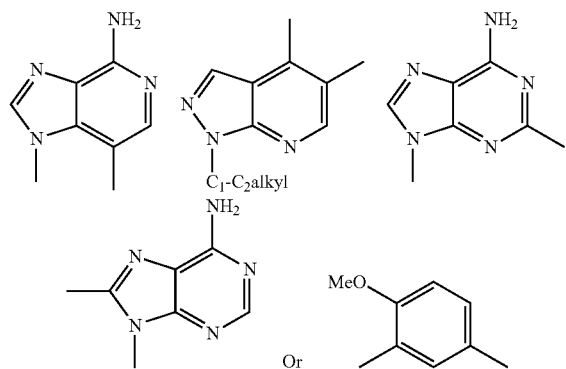

and
W is a group of formula

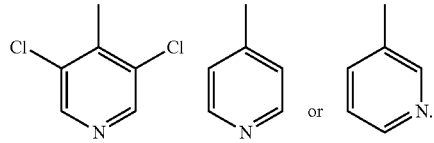

18. A compound according to claim 1, wherein X is —$CH_2$—$CH_2$—$CH_2$— or —$CH_2$—$CH_2$—$CH_2$—$CH_2$— or, —$CH_2$—$CH_2$—$CH_2$—NH— or —$CH_2$—$CH_2$—$CH_2$—O— linked to the residue Q via the NH group or O atom, respectively.

19. A compound according to claim 1 having one of the formulae:

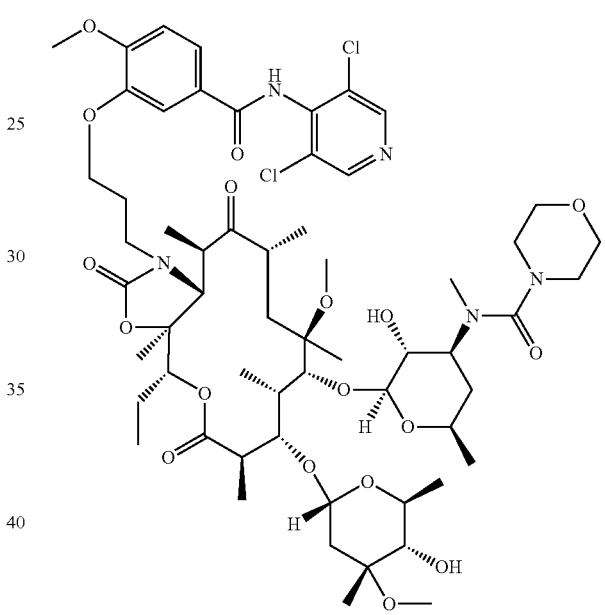

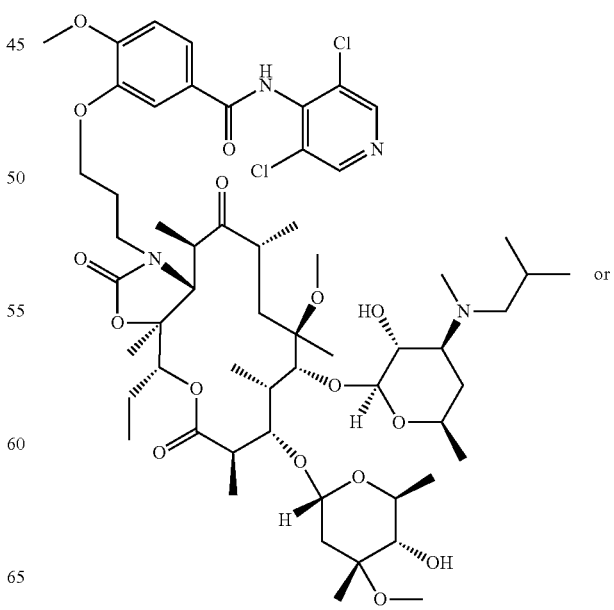

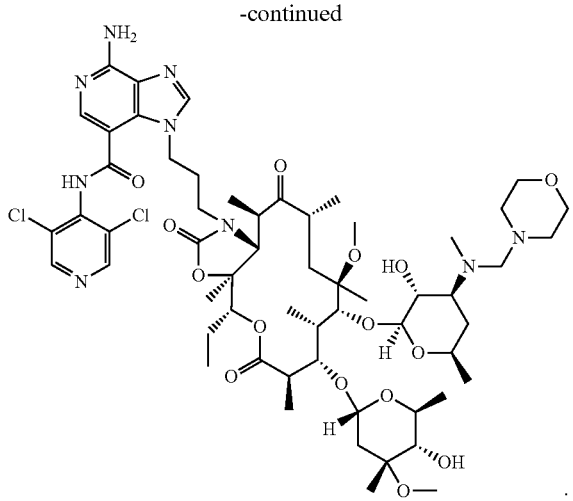
20. The compound according to claim 1 having substantially no antibacterial activity so as not to create antibiotic resistant bacteria.
21. A medicament, comprising a compound according to claim 1 and a pharmaceutically acceptable carrier.
22. The compound according to claim 1, wherein said compound is:
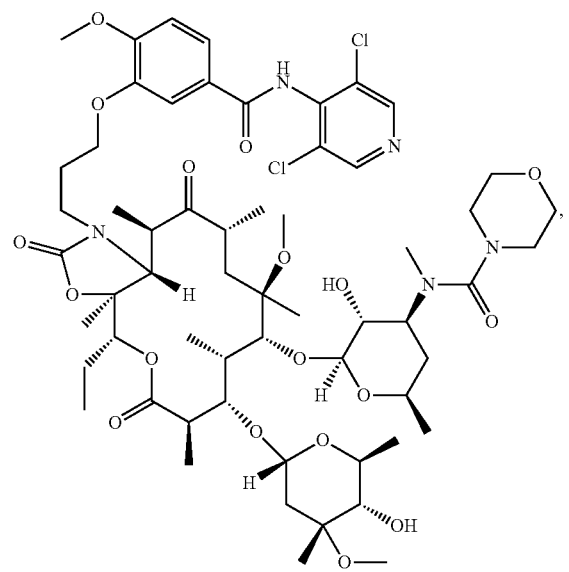
,
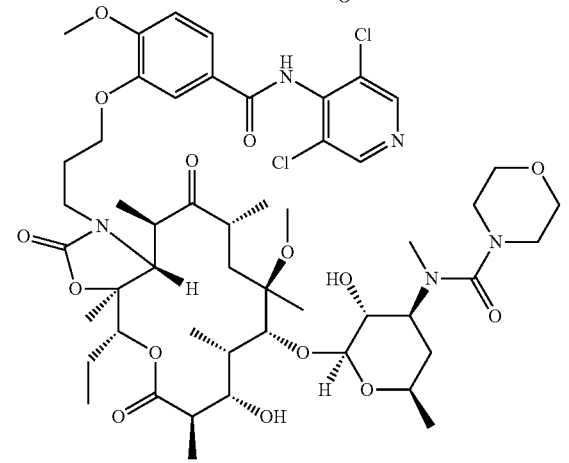
or
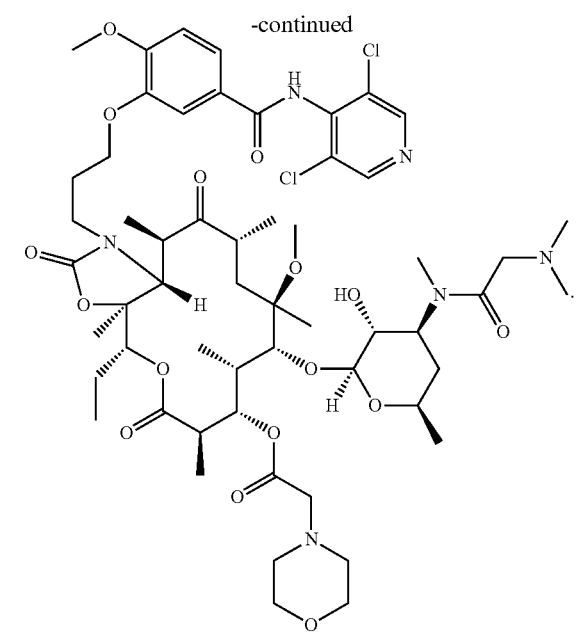
,
23. The compound according to claim 1, wherein said compound is:
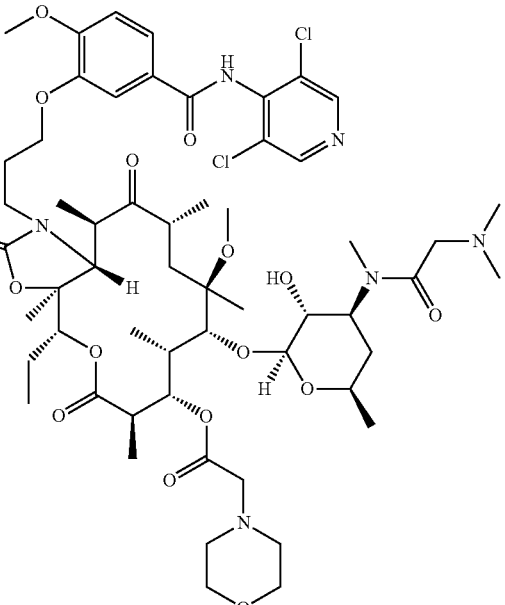
or
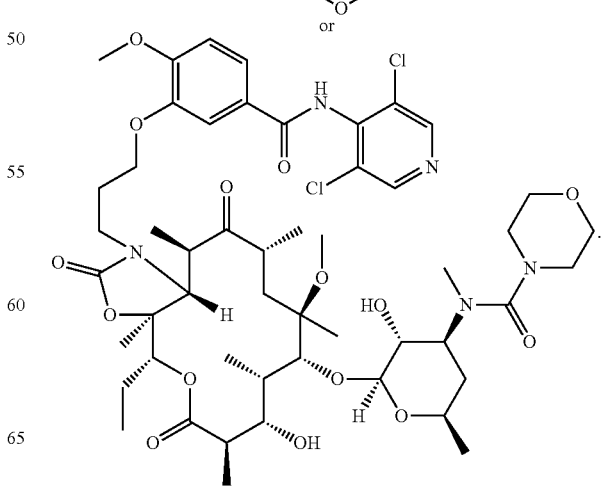
.

24. The compound according to claim 23, wherein said compound is:
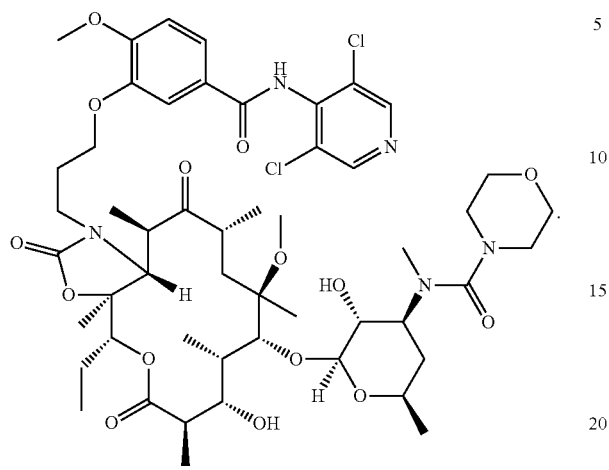
25. The compound according to claim 1, wherein W is heterocyclyl.
* * * * *